(12) United States Patent
Shishido et al.

(10) Patent No.: US 9,979,914 B2
(45) Date of Patent: May 22, 2018

(54) IMAGING DEVICE

(71) Applicant: Panasonic Intellectual Property Management Co., Ltd., Osaka (JP)

(72) Inventors: Sanshiro Shishido, Osaka (JP); Masashi Murakami, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days. days.

(21) Appl. No.: 15/451,567

(22) Filed: Mar. 7, 2017

(65) Prior Publication Data

US 2017/0272677 A1 Sep. 21, 2017

(30) Foreign Application Priority Data

Mar. 17, 2016 (JP) ................................ 2016-053281

(51) Int. Cl.
*H04N 3/14* (2006.01)
*H04N 5/335* (2011.01)
(Continued)

(52) U.S. Cl.
CPC ......... *H04N 5/3742* (2013.01); *H01L 27/148* (2013.01); *H04N 5/3696* (2013.01); *H04N 5/378* (2013.01); *H04N 5/363* (2013.01)

(58) Field of Classification Search
CPC .... H04N 5/3742; H04N 5/378; H04N 5/3696; H04N 5/363; H01L 27/148
(Continued)

(56) References Cited

U.S. PATENT DOCUMENTS 9,673,258 B2* 6/2017 Choo ................... H01L 51/424
2011/0007196 A1* 1/2011 Yamashita ........ H01L 27/14609
348/294

(Continued)

FOREIGN PATENT DOCUMENTS

JP 2012-501608 1/2012
JP 2012-216692 11/2012
(Continued)

OTHER PUBLICATIONS

K. Yasutomi et al., "A 0.3mm-Resolution Time-of-Flight CMOS Range Imager with Column-Gating Clock-Skew Calibration", ISSCC2014, Dig. pp. 132-133, Feb. 2014.

*Primary Examiner* — Yogesh Aggarwal
(74) *Attorney, Agent, or Firm* — McDermott Will & Emery LLP

(57) ABSTRACT

An imaging device includes first and second pixel cells. The first and second pixel cells each include: a photoelectric converter that generates charge; a first charge transfer channel that has a first end electrically connected to the photoelectric converter, and a second end, the charge transfer channel transferring the charge in a direction from the first end toward the second end; a second charge transfer channel that branches from a position of the charge transfer channel, the second charge transfer channel transferring at least a part of the charge; and a charge accumulator that accumulates charge transferred via the second charge transfer channel. Distances from the first end to the position in the direction of the first and second pixel cells are different from each other.

15 Claims, 21 Drawing Sheets

(51) Int. Cl.
    *H04N 5/374*     (2011.01)
    *H04N 5/369*     (2011.01)
    *H04N 5/378*     (2011.01)
    *H01L 27/148*     (2006.01)
    *H04N 5/363*     (2011.01)

(58) Field of Classification Search
    USPC ........ 348/294–324; 250/208.1; 257/290–292
    See application file for complete search history.

(56) References Cited

U.S. PATENT DOCUMENTS

| | | | |
|---|---|---|---|
| 2011/0317053 A1 | 12/2011 | Hiramoto et al. | |
| 2012/0127542 A1* | 5/2012 | Okada | H04N 1/40056 |
| | | | 358/474 |
| 2012/0248291 A1 | 10/2012 | Kamiyama et al. | |
| 2014/0042507 A1* | 2/2014 | Iwata | H01L 27/14612 |
| | | | 257/294 |
| 2016/0173802 A1* | 6/2016 | Matsuo | H04N 5/372 |
| | | | 348/322 |
| 2016/0247843 A1* | 8/2016 | Iwata | H01L 27/14603 |

FOREIGN PATENT DOCUMENTS

| | | |
|---|---|---|
| WO | 2010/025331 | 3/2010 |
| WO | 2011/043045 | 4/2011 |

* cited by examiner

IMAGING DEVICE

BACKGROUND

1. Technical Field

The present disclosure relates to an imaging device.

2. Description of the Related Art

There is demand for an imaging element that is capable of high-speed operation in distance measurements, ultra-high-speed imaging, and the like, in which fluorescence-lifetime imaging microscopy (FLIM) and the time-of-flight method are used. For example, in fluorescence-lifetime imaging microscopy, an optical pulse is irradiated onto a sample, and fluorescence emitted from the sample is repeatedly detected at extremely short time intervals of the order of several nanoseconds. If the temporal resolution in measurement can be improved, it is expected that new findings can be obtained in relation to observation subjects.

The temporal resolution in measurement for which an imaging element is used is dependent upon the operating speed of each pixel. For example, in detection using a complementary metal-oxide semiconductor (CMOS) type of imaging element, an operation is carried out repeatedly in which the discharge of charge within a photodiode (a photodiode reset), the accumulation of charge produced by exposure to light, and the transfer of charge to a floating diffusion is regarded as one cycle. In other words, the temporal resolution in measurement is dependent upon the time required for this cycle. In the aforementioned cycle, in particular, the time required for the discharge of charge from the pixels and the transfer of charge to the floating diffusion greatly affects the high-speed operation of an imaging element.

K. Yasutomi, et al., "A 0.3 mm-Resolution Time-of-Flight CMOS Range Imager with Column-Gating Clock-Skew Calibration", ISSCC2014, Dig. pp. 132-133 proposes a configuration in which a discharge gate is provided between a photodiode and a drain for discharging charge. In the aforementioned document, a pixel having this kind of configuration is referred to as a draining-only modulation (DOM) pixel. In a DOM pixel, when the discharge gate is in an open state, charge within the photodiode is discharged. Meanwhile, when the discharge gate is in a closed state, charge within the photodiode can be transferred to a floating diffusion. In a DOM pixel, the time required for a reset is practically zero, thereby achieving an improvement in temporal resolution.

SUMMARY

Further improvement in temporal resolution is required.

A non-limiting and exemplary embodiment of the present disclosure provides the following.

In one general aspect, the techniques disclosed here feature an imaging device comprising a first pixel cell and a second pixel cell. The first pixel cell includes: a first photoelectric converter that generates first charge; a first charge transfer channel that has a first end electrically connected to the first photoelectric converter, and a second end, the first charge transfer channel transferring the first charge in a first direction from the first end toward the second end; a second charge transfer channel that branches from a first position of the first charge transfer channel, the second charge transfer channel transferring at least a part of the first charge; and a first charge accumulator that accumulates charge transferred via the second charge transfer channel. The second pixel cell includes: a second photoelectric converter that generates second charge; a third charge transfer channel that has a third end electrically connected to the second photoelectric converter, and a fourth end, the third charge transfer channel transferring the second charge in a second direction from the third end toward the fourth end; a fourth charge transfer channel that branches from a second position of the third charge transfer channel, the fourth charge transfer channel transferring at least a part of the second charge; and a second charge accumulator that accumulates charge transferred via the fourth charge transfer channel. A distance from the first end to the first position in the first direction is different from a distance from the third end to the second position in the second direction.

General or specific aspects may be realized by an element, a device, a system, an integrated circuit, or a method. Furthermore, general or specific aspects may be realized by an arbitrary combination of an element, a device, a system, an integrated circuit, and a method.

Additional benefits and advantages of the disclosed embodiments will be apparent from the specification and Figures. The benefits and/or advantages may be individually provided by the various embodiments or features disclosed in the specification and Figures, and need not all be provided in order to obtain one or more of the same.

DETAILED DESCRIPTION

Figure 1:
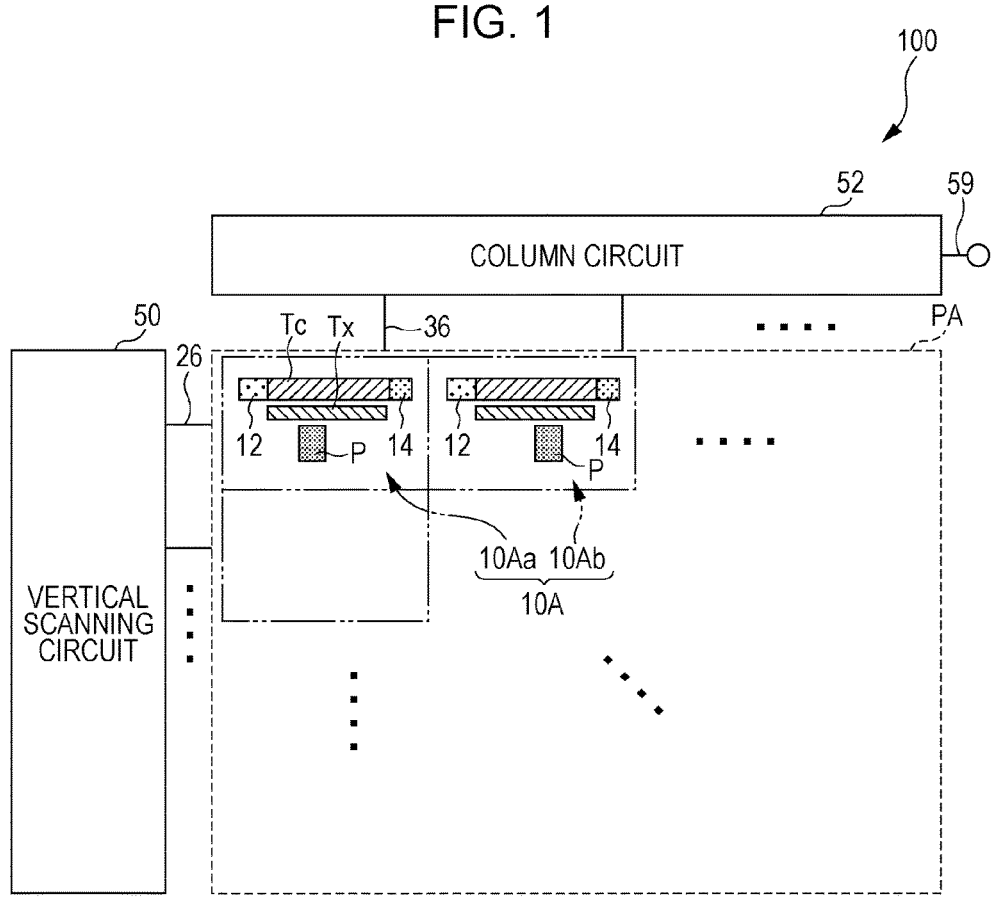
FIG. 1 is a drawing depicting an overview of an exemplary circuit configuration of an imaging device according to a first embodiment of the present disclosure.

In the aforementioned DOM pixel, it is necessary for the charge generated by the photodiode to be moved to the floating diffusion every time the discharge gate is closed. Therefore, in an imaging element in which the DOM pixel is applied, temporal resolution is dependent upon the response speed of the discharge gate and the transfer speed of charge from the photodiode to the floating diffusion. The transfer speed of charge from the photodiode to the floating diffusion is restricted by the mobility within a silicon (Si) substrate. Consequently, it is difficult to further improve temporal resolution with the conventional method in which charge is transferred to the floating diffusion every time a reset occurs and the charge accumulated in the floating diffusion is read out.

An overview of an aspect of the present disclosure is as follows.

[Item 1]

An imaging device comprising a first pixel cell and a second pixel cell, wherein the first pixel cell includes:

a first photoelectric converter that generates first charge;

a first charge transfer channel that has a first end electrically connected to the first photoelectric converter, and a second end, the first charge transfer channel transferring the first charge in a first direction from the first end toward the second end;

a second charge transfer channel that branches from a first position of the first charge transfer channel, the second charge transfer channel transferring at least a part of the first charge; and a first charge accumulator that accumulates charge transferred via the second charge transfer channel, the second pixel cell includes:

a second photoelectric converter that generates second charge;

a third charge transfer channel that has a third end electrically connected to the second photoelectric converter, and a fourth end, the third charge transfer channel transferring the second charge in a second direction from the third end toward the fourth end;

a fourth charge transfer channel that branches from a second position of the third charge transfer channel, the fourth charge transfer channel transferring at least a part of the second charge; and a second charge accumulator that accumulates charge transferred via the fourth charge transfer channel, and a distance from the first end to the first position in the first direction is different from a distance from the third end to the second position in the second direction.

[Item 2]

The imaging device according to item 1, wherein the first pixel cell includes a first gate that switches between transferring and blocking the at least the part of the first charge to the second charge transfer channel, and the second pixel cell includes a second gate that switches between transferring and blocking the at least the part of the second charge to the fourth charge transfer channel.

[Item 3]

The imaging device according to item 2, further comprising a controller that causes the first gate and the second gate to be changed from blocking to transferring at a same timing.

[Item 4]

The imaging device according to item 2, wherein the first gate includes a first gate electrode located on the second charge transfer channel, the second gate includes a second gate electrode located on the fourth charge transfer channel, and the first gate electrode is electrically connected to the second gate electrode.

[Item 5]

The imaging device according to any one of items 1 to 4, wherein the first pixel cell includes a first gate that switches between transferring and blocking charge from the first photoelectric converter to the first charge transfer channel, and the second pixel cell includes a second gate that switches between transferring and blocking charge from the second photoelectric converter to the third charge transfer channel.i

[Item 6]

The imaging device according to any one of items 1 to 5, wherein the first pixel cell includes a first drain electrically connected to the second end of the first charge transfer channel, and the second pixel cell includes a second drain electrically connected to the fourth end of the third charge transfer channel.

[Item 7]

The imaging device according to any one of items 1 to 6, wherein the first pixel cell includes:

a first drain electrically connected to a third position of the first charge transfer channel; and a first gate that switches between transferring and blocking charge from the third position to the first drain, the second pixel cell includes:

a second drain electrically connected to a fourth position of the second charge transfer channel; and a second gate that switches between transferring and blocking charge from the fourth position to the second drain, a distance from the first end to the third position in the first direction is the same as a distance from the third end to the fourth position in the second direction, a distance from the first end to the third position in the first direction is less than a distance from the first end to the first position in the first direction, and a distance from the third end to the fourth position in the second direction is less than a distance from the third end to the second position in the second direction.

[Item 8]

The imaging device according to any one of items 1 to 7, wherein the first pixel cell includes a third charge accumulator that is electrically connected to the second end of the first charge transfer channel, the third charge accumulator accumulating charge transferred via the first charge transfer channel, and the second pixel cell includes a fourth charge accumulator that is electrically connected to the fourth end of the third charge transfer channel, the fourth charge accumulator accumulating charge transferred via the third charge transfer channel.

[Item 9]

The imaging device according to item 1, wherein the first pixel cell includes:

a fifth charge transfer channel that branches from a third position of the first charge transfer channel, the fifth charge transfer channel transferring at least a part of the first charge;

a first gate that switches between transferring and blocking charge in the fifth charge transfer channel;

a third charge accumulator that accumulates charge transferred via the fifth charge transfer channel;

a sixth charge transfer channel that branches from a fourth position of the first charge transfer channel, the sixth charge transfer channel transferring at least a part of the first charge;

a second gate that switches between transferring and blocking charge in the sixth charge transfer channel; and a fourth charge accumulator that accumulates charge transferred via the sixth charge transfer channel, and a distance from the first end to the third position in the first direction is different from a distance from the first end to the fourth position in the first direction.

[Item 10]

The imaging device according to item 9, wherein the first charge transfer channel is located, in plan view, between the third and fourth charge accumulators and the first charge accumulator.

[Item 11]

The imaging device according to item 9 or 10, wherein the first pixel cell includes:

a third gate that switches between transferring and blocking the first charge from the first photoelectric converter to the first charge transfer channel;

a first drain electrically connected to the second end of the first charge transfer channel; and a fourth gate that is located between the first charge transfer channel and the first drain, the fourth gate switching between transferring and blocking charge from the first charge transfer channel to the first drain.

[Item 12]

The imaging device according to any one of items 9 to 11, wherein the first pixel cell includes:

a fifth charge accumulator electrically connected to the first charge accumulator;

a third gate that switches between transferring and blocking charge accumulated in the first charge accumulator from the first charge accumulator to the fifth charge accumulator; and a read-out circuit electrically connected to the fifth charge accumulator.

[Item 13]

The imaging device according to any one of items 9 to 11, wherein the first pixel cell includes:

a capacitor electrically connected to the first charge accumulator; and a read-out circuit electrically connected to the first charge accumulator.

[Item 14]

The imaging device according to any one of items 1 to 13, comprising first pixel cells and second pixel cells, the first pixel cell being one of the first pixel cells, the second pixel cell being one of the second pixel cells, wherein the first pixel cells and the second pixel cells are arranged two-dimensionally in a row direction and a column direction, the first pixel cells are arranged in one of the row direction and the column direction, and the second pixel cells are arranged in the one of the row direction and the column direction.

[Item 15]

The imaging device according to any one of items 1 to 14, wherein the first charge transfer channel does not have a gate between the first end and the second end, and the second charge transfer channel does not have a gate between the third end and the fourth end.

[Item 16]

An imaging device provided with a first pixel cell and a second pixel cell, wherein the first pixel cell includes:

a first photoelectric converter;

a first charge transfer channel that transfers charge generated by the first photoelectric converter;

a second charge transfer channel that branches from midway along the first charge transfer channel; and a first charge accumulator that accumulates charge transferred via the second charge transfer channel, from among the charge generated by the first photoelectric converter, the second pixel cell includes:

a second photoelectric converter;

a third charge transfer channel that transfers charge generated by the second photoelectric converter;

a fourth charge transfer channel that branches from midway along the third charge transfer channel; and a second charge accumulator that accumulates charge transferred via the fourth charge transfer channel, from among the charge generated by the second photoelectric converter, and the distance along the first charge transfer channel, from the first photoelectric converter to the branching point of the first charge transfer channel and the second charge transfer channel is different from the distance along the third charge transfer channel, from the second photoelectric converter to the branching point of the third charge transfer channel and the fourth charge transfer channel.

According to the configuration of item 16, detection in time windows that start at different times can be executed simultaneously between the first pixel cell and the second pixel cell.

[Item 17]

The imaging device according to item 16, wherein the first pixel cell includes a first gate that switches between transferring and blocking charge via the second charge transfer channel, and the second pixel cell includes a second gate that switches between transferring and blocking charge via through the fourth charge transfer channel.

According to the configuration of item 17, a portion of the signal charge moving within the first charge transfer channel can be extracted and accumulated in the first charge accumulator, and a portion of the signal charge moving within the third charge transfer channel can be extracted and accumulated in the second charge accumulator.

[Item 18]

The imaging device according to any one of items 16 or 17, wherein the timing at which charge is transferred to the first charge accumulator via the second charge transfer channel, and the timing at which charge is transferred to the second charge accumulator via the fourth charge transfer channel are the same.

[Item 19]

The imaging device according to any one of items 16 to 18, wherein the first pixel cell includes:

a plurality of third charge accumulators arranged along the first charge transfer channel, on the opposite side of the first charge transfer channel to the first charge accumulator;

a plurality of fifth charge transfer channels branching from midway along the first charge transfer channel, and having one from among the plurality of third charge accumulators arranged at an end of each of the plurality of fifth charge transfer channels; and at least one third gate that switches between transferring and blocking charge via at least one of the plurality of fifth charge transfer channels, and the second pixel cell includes:

a plurality of fourth charge accumulators arranged along the third charge transfer channel, on the opposite side of the third charge transfer channel to the second charge accumulator;

a plurality of sixth charge transfer channels branching from midway along the third charge transfer channel, and having one from among the plurality of fourth charge accumulators arranged at an end of each of the plurality of sixth charge transfer channels; and at least one fourth gate that switches between transferring and blocking charge via at least one of the plurality of sixth charge transfer channels.

According to the configuration of item 19, detection in time windows that start at different times can be executed simultaneously.

[Item 20]

The imaging device according to any one of items 16 to 19, wherein the first pixel cell includes a fifth gate that switches between transferring and blocking charge from the first photoelectric converter to the first charge transfer channel, and the second pixel cell includes a sixth gate that switches between transferring and blocking charge from the second photoelectric converter to the third charge transfer channel.

According to the configuration of item 20, the timings at which the transfer of signal charge from the photoelectric converter is started and ended can be electrically controlled.

[Item 21]

The imaging device according to any one of items 16 to 20, wherein the first pixel cell includes a first drain located at an end of the first charge transfer channel, and the second pixel cell includes a second drain located at an end of the third charge transfer channel.

According to the configuration of item 21, the signal charge generated by the photoelectric converter can be moved from the photoelectric converter toward the drain.

[Item 22]

The imaging device according to any one of items 16 to 20, wherein the first pixel cell includes a third charge accumulator that is located at an end of the first charge transfer channel, and accumulates charge transferred via the first charge transfer channel, and the second pixel cell includes a fourth charge accumulator that is located at an end of the third charge transfer channel, and accumulates charge transferred via the third charge transfer channel.

According to the configuration of item 22, charge can be distributed at an arbitrary ratio between two charge accumulators formed within pixel cells.

[Item 23]

The imaging device according to item 19, wherein the first pixel cell includes:

a fifth gate that switches between transferring and blocking charge from the first photoelectric converter to the first charge transfer channel;

a first drain located at an end of the first charge transfer channel; and a sixth gate that is arranged between the end of the first charge transfer channel and the first drain, and switches between transferring and blocking charge from the end of the first charge transfer channel to the first drain, and the second pixel cell includes:

a seventh gate that switches between transferring and blocking charge from the second photoelectric converter to the third charge transfer channel;

a second drain located at an end of the third charge transfer channel; and an eighth gate that is arranged between the end of the third charge transfer channel and the second drain, and switches between transferring and blocking charge from the end of the third charge transfer channel to the second drain.

According to the configuration of item 23, it is possible for charge to be read out from each of a plurality of charge accumulators by a single signal detection circuit in each pixel cell, which is therefore advantageous for the miniaturization of pixel cells.

[Item 24]

The imaging device according to item 23, wherein the first pixel cell includes:

a fifth charge accumulator;

a ninth gate that switches between transferring and blocking, to the fifth charge accumulator, charge accumulated in the first charge accumulator; and a first read-out circuit that reads out charge transferred to the fifth charge accumulator, and the second pixel cell includes:

a sixth charge accumulator;

a tenth gate that switches between transferring and blocking, to the sixth charge accumulator, charge accumulated in the second charge accumulator; and a second read-out circuit that reads out charge transferred to the sixth charge accumulator.

According to the configuration of item 24, the effect of noise such as reset noise can be suppressed.

[Item 25]

An imaging device that has an arrangement of a plurality of pixel blocks that each include two or more pixel cells, wherein each of the two or more pixel cells within each pixel block includes:

a photoelectric converter;

a first charge transfer channel that transfers charge generated by the photoelectric converter;

a second charge transfer channel that branches from midway along the first charge transfer channel; and a charge accumulator that accumulates charge transferred via the second charge transfer channel, from among the charge generated by the photoelectric converter, and the distance along the first charge transfer channel, from the photoelectric converter to the branching point of the first charge transfer channel and the second charge transfer channel is different among the two or more pixel cells.

According to the configuration of item 25, it is possible for a plurality of items of image data corresponding to a plurality of mutually different time windows to be acquired at high speed with a single exposure.

[Item 26]

The imaging device according to item 25, wherein the plurality of pixel blocks are arranged in a first direction, each of the plurality of pixel blocks includes the two or more pixel cells arranged in a second direction that is different from the first direction, and the distance is common among the pixel cells arranged side-by-side in the first direction.

According to the configuration of item 26, each row in a pixel array that includes a plurality of pixel cells can be used as a line sensor.

Hereinafter, embodiments of the present disclosure will be described in detail with reference to the drawings. It should be noted that the embodiments described hereinafter all represent general or specific examples. The numerical values, the shapes, the materials, the constituent elements, the arrangement of the constituent elements, the mode of connection, the steps, and the order of the steps and so forth given in the following embodiments are examples and are not intended to restrict the present disclosure. The various aspects described in the present specification may be combined with each other provided there are no resulting inconsistencies. Furthermore, from among the constituent elements in the following embodiments, constituent elements that are not described in the independent claims indicating the most significant concepts are described as optional constituent elements. In the following description, constituent elements having substantially the same functions may be denoted by common reference numerals, and descriptions thereof may be omitted.

First Embodiment

FIG. 1 depicts an overview of an exemplary circuit configuration of an imaging device according to a first embodiment of the present disclosure. An imaging device 100 exemplified in FIG. 1 has a pixel array PA that is an arrangement of a plurality of pixel cells, and has peripheral circuits that include a vertical scanning circuit 50 and a column circuit 52. A plurality of pixel cells 10A within the pixel array PA are typically formed on a semiconductor substrate. The pixel cells 10A are arranged in a one-dimensional or two-dimensional manner to thereby form an imaging region (photosensitive region). In this case, an example is given in which the plurality of pixel cells 10A, which includes pixel cells 10Aa and 10Ab, are arranged in a two-dimensional manner. In the configuration exemplified in FIG. 1, the pixel cells 10A are arranged in the form of a matrix that includes a plurality of rows and columns. Needless to say, the number and arrangement of the pixel cells in the pixel array PA is not restricted to the example depicted in FIG. 1. For example, if the pixel cells 10A are arranged in a one-dimensional manner, it is possible for the imaging device 100 to be used as a line sensor.

Each of the pixel cells 10A has a photoelectric converter 12 and a charge accumulator P that temporarily accumulates at least a portion of charge that is generated by the photoelectric converter 12. In the configuration exemplified in FIG. 1, each of the pixel cells 10A also has a drain 14 for discharging at least a portion of the charge generated by the photoelectric converter 12 to the outside. It should be noted that FIG. 1 is merely a schematic drawing for illustration purposes, and the size of each section in the drawing does not necessarily reflect the actual size. Likewise also in other drawings, the size of an element depicted in the drawings may not match the actual size of the element in question.

As described in detail later on, each of the pixel cells 10A also has a first charge transfer channel that transfers the charge generated by the photoelectric converter 12, and a second charge transfer channel that branches from midway along the first charge transfer channel. In this example, the first charge transfer channel is formed as a charge transfer channel that joins the photoelectric converter 12 and the drain 14. In other words, the photoelectric converter 12 is located at one end of the first charge transfer channel, and the drain 14 is located at the other end of the first charge transfer channel. Alternatively, it may be said that the photoelectric converter 12 is connected to one end of the first charge transfer channel, and the drain 14 is connected to the other end of the first charge transfer channel. In this case, each of the pixel cells 10A has a control electrode Tc, and the control electrode Tc is arranged on the first charge transfer channel. The second charge transfer channel is formed as a charge transfer channel that joins the first charge transfer channel and a charge accumulator P. In other words, the charge accumulator P is located at an end of the second charge transfer channel. A transfer gate electrode Tx is arranged between the control electrode Tc and the charge accumulator P.

In the embodiments of the present disclosure, the pixel array PA includes two or more pixel cells having mutually different distances from the photoelectric converter 12 to the branching point of the first charge transfer channel and the second charge transfer channel, in the direction in which the photoelectric converter 12 and the drain 14 are joined. Typically, between these pixel cells, the distances between the photoelectric converter 12 and the charge accumulator P in the direction in which the photoelectric converter 12 and the drain 14 are joined are mutually different. For example, in the configuration depicted in FIG. 1, the distances between the photoelectric converter 12 and the charge accumulator P in the direction in which the photoelectric converter 12 and the drain 14 are joined are mutually different between the pixel cell 10Aa and the pixel cell 10Ab. Consequently, the charge transfer distances from the photoelectric converter 12 to the charge accumulator P are mutually different between the pixel cell 10Aa and the pixel cell 10Ab. As described later on, since two or more pixel cells (in this case, the pixel cells 10Aa and 10Ab) having mutually different charge transfer distances from the photoelectric converter 12 to the charge accumulator P are arranged within the pixel array PA, it is possible for detection in time windows that start at different times to be executed simultaneously among these pixel cells.

Each of the pixel cells 10A within the pixel array PA is controlled by a column scanning circuit or a row scanning circuit arranged outside of the imaging region, for example. In the configuration depicted in FIG. 1, gate control lines 26 that are provided for each row of the plurality of pixel cells 10A is connected to the vertical scanning circuit 50. Each of the gate control lines 26 is connected to the transfer gate electrodes Tx within the pixel cells 10A of the corresponding row. Consequently, the vertical scanning circuit 50 is able to control the pixel cells 10A within the pixel array PA in row units by controlling voltages applied to the gate control lines 26. In this kind of configuration, the vertical scanning circuit 50 can be referred to as a row scanning circuit. Needless to say, instead of the vertical scanning circuit 50, a column scanning circuit may be arranged in the row direction in the pixel array PA, and the plurality of pixel cells 10A may be controlled by the column scanning circuit via control lines arranged for each column of the plurality of pixel cells 10A. It should be noted that in the present specification, the row direction means the direction in which rows extend, and the column direction means the direction in which columns extend. For example, in FIG. 1, the row direction is the lateral direction in the page space, and the column direction is the vertical direction in the page space.

Meanwhile, the column circuit 52 is connected to vertical signal lines 36 that are provided for each column of the plurality of pixel cells 10A. The output of the pixel cells 10A belonging to a certain column within the pixel array PA is read out to the column circuit 52 via one vertical signal line 36 corresponding to said column, from among the plurality of vertical signal lines 36. The column circuit 52 may have sets of a column signal processing circuit (also referred to as a "row signal accumulation circuit") and a load circuit. The column signal processing circuit and the load circuit are provided for each column corresponding to each of the plurality of vertical signal lines 36. The load circuit forms part of a source follower, and the column signal processing circuit performs noise-suppression signal processing represented by correlated double sampling, analog-digital conversion (AD conversion), and the like. Signals from the plurality of column signal processing circuits are sequentially read out to a horizontal common signal line 59.

(Typical Example of the Configuration of the Pixel Cells 10A)

Figure 2:
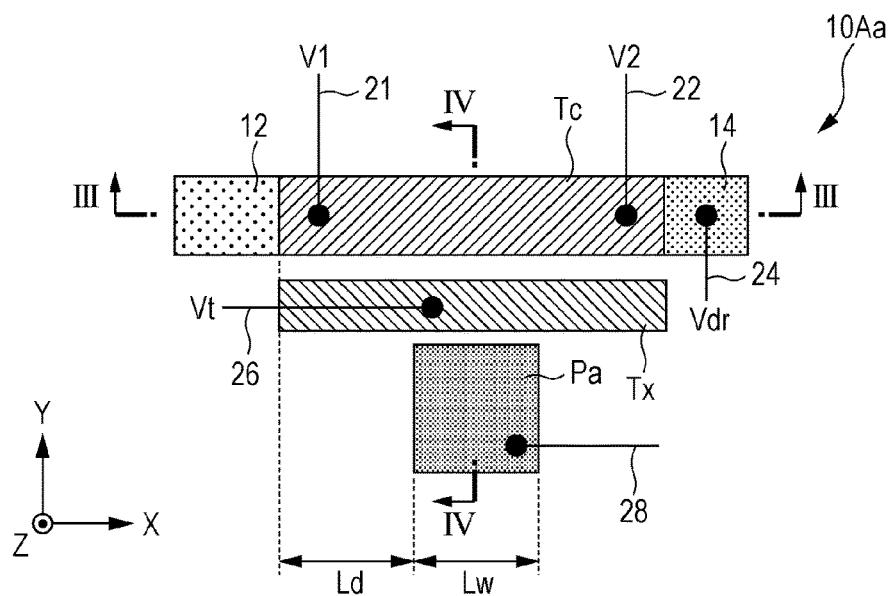
FIG. 2 is a schematic plan view of a pixel cell.
Figure 3:
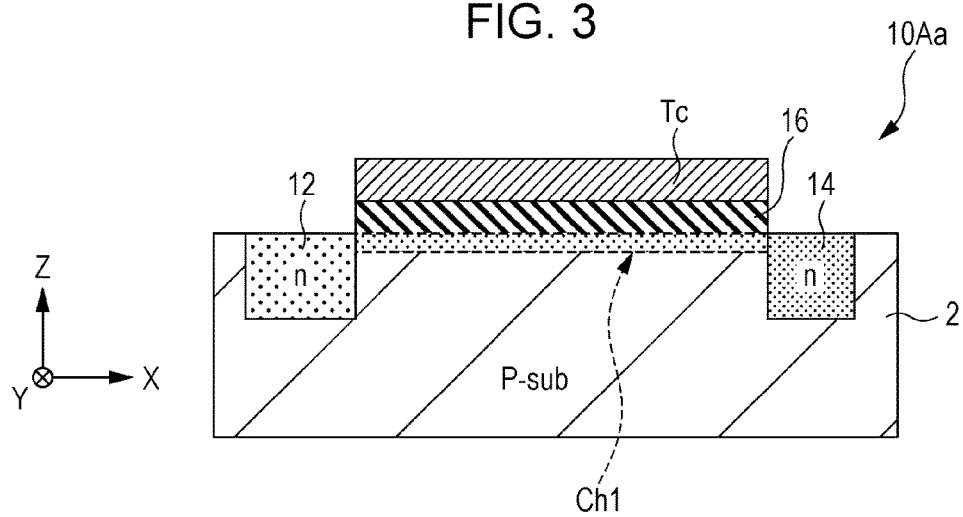
FIG. 3 is a cross-sectional view along the III-III line depicted in FIG. 2.
Figure 4:
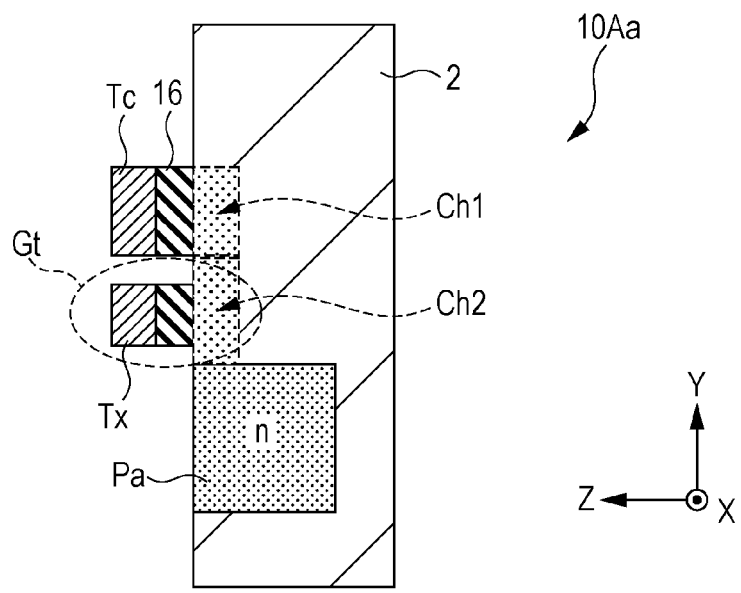
FIG. 4 is a cross-sectional view along the IV-IV line depicted in FIG. 2.

FIGS. 2 to 4 schematically depict an example of the pixel structure in the pixel cells 10A. In this case, an example of the pixel structure in the pixel cell 10Aa is given as a representative example from among the pixel cells 10A. FIG. 2 schematically depicts the arrangement of each section making up the pixel cell 10Aa when seen from the direction normal to the imaging surface. FIG. 3 schematically depicts a cross-sectional view along the III-III line depicted in FIG. 2. FIG. 4 schematically depicts a cross-sectional view along the IV-IV line depicted in FIG. 2. In FIGS. 2 to 4, arrows indicating the mutually orthogonal X direction, Y direction, and Z direction are depicted for reference. In this case, the Z direction coincides with the direction normal to the imaging surface. Arrows indicating the X direction, Y direction, and Z direction are sometimes also depicted in other drawings. It should be noted that in order to avoid the drawings becoming complex, the depiction of wiring such as the gate control lines 26 is sometimes omitted hereinafter.

As depicted in FIG. 2, in this example, the photoelectric converter 12 and the drain 14 are arranged in the X direction with space therebetween. The photoelectric converter 12 includes a photoelectric conversion element that is capable of receiving incident light and generating charge (may be referred to as "signal charge" hereinafter). In this case, a photodiode formed on a semiconductor substrate is given as an example of a photoelectric conversion element. Hereinafter, the photoelectric converter 12 is referred to as a photodiode 12 for convenience. The photodiode 12, the drain 14, and the aforementioned charge accumulator P may be impurity regions (for instance, diffusion regions) formed in the semiconductor substrate.

In this example, the control electrode Tc is arranged on a region that joins the photodiode 12 and the drain 14. As mentioned above, the first charge transfer channel is formed as a charge transfer channel that joins the photoelectric converter 12 and the drain 14. Consequently, in the configuration depicted in FIG. 2, it may be said that the arrangement of the first charge transfer channel substantially coincides with the arrangement of the control electrode Tc.

The control electrode Tc is typically formed of polysilicon imparted with conductivity by being doped with an impurity. In this example, a power line 21 connected to a power source that is not depicted is connected in the vicinity of the end section of the photodiode 12 side of the control electrode Tc. Furthermore, a power line 22 connected to a power source that is not depicted is connected in the vicinity of the end section of the drain 14 side of the control electrode Tc. The control electrode Tc can be configured in such a way as to be capable of independently controlling the potential of both end sections during operation of the imaging device 100.

The drain 14 located in the vicinity of one end section of the control electrode Tc is connected to a power line 24 connected to a power source that is not depicted. During operation of the imaging device 100, the drain 14 receives the supply of a predetermined voltage Vdr via the power line 24, and the potential thereof is thereby fixed.

The charge accumulator P (in this case, a charge accumulator Pa) is formed spaced apart in the Y direction from the region in which the control electrode Tc is arranged. The charge accumulator Pa functions as a storage that temporarily accumulates signal charge. The charge accumulator Pa has a read-out line 28 connected thereto. The read-out line 28 is connected to a signal detection circuit, which is not depicted and includes an amplification transistor or the like, and a signal corresponding to the amount of charge accumulated in the charge accumulator Pa is read out to the corresponding vertical signal line 36 via the signal detection circuit. Although not depicted, the charge accumulator Pa can be connected to a reset voltage line which supplies a reset voltage that resets the potential of the charge accumulator Pa.

The gate control line 26 connected to the vertical scanning circuit 50 is connected to the transfer gate electrode Tx arranged between the control electrode Tc and the charge accumulator Pa. The potential of the transfer gate electrode Tx is controlled by means of a gate control voltage Vt supplied from the vertical scanning circuit 50 via the gate control line 26. The transfer gate electrode Tx can be formed of a metal such as aluminum or copper, a metal nitride, or polysilicon.

Other pixel cells 10A within the pixel array PA have schematically the same configuration as that of the pixel cell 10Aa. However, at least one of the pixel cells 10A within the pixel array PA differs from the pixel cell 10Aa in terms of the distance Ld from the photodiode 12 to the charge accumulator P in the direction along the first charge transfer channel.

As schematically depicted in FIG. 1, in this case, the aforementioned distance Ld in the pixel cell 10Ab differs from the distance Ld in the pixel cell 10Aa. In this example, the distance Ld in the pixel cell 10Ab is larger than the distance Ld in the pixel cell 10Aa. It should be noted that both arrows Lw in FIG. 2 indicate the length (width) of the charge accumulator P (in this case, the charge accumulator Pa), in the direction along the first charge transfer channel.

Reference will now be made to FIGS. 3 and 4. In this example, the photodiode 12, the drain 14, and the charge accumulator Pa are formed within a semiconductor substrate 2 such as a silicon (Si) substrate. Hereinafter, a p-type silicon substrate is given as an example of the semiconductor substrate 2. In this case, the photodiode 12 is formed by forming an N-type region in the p-type silicon substrate. Furthermore, in this case, other N-type regions formed in the p-type silicon substrate are used as the drain 14 and the charge accumulator Pa. Two adjacent pixel cells 10A are electrically isolated by an element isolation region (in this case, a P-type region that is not depicted) formed in the semiconductor substrate 2. The semiconductor substrate 2 is not restricted to a substrate in which the entirety thereof is a semiconductor layer, and may be an insulation substrate in which a semiconductor layer is provided on the surface on the imaging surface side.

As described in detail later on, during operation of the imaging device 100, the signal charge generated by the photodiode 12 moves within the semiconductor substrate 2 from the photodiode 12 toward the drain 14 due to the potential of the drain 14 being fixed at a predetermined potential, for example. In other words, the region between the photodiode 12 and the drain 14 within the semiconductor substrate 2 functions as the first charge transfer channel (referred to simply as a "charge transfer channel Ch1" hereinafter) that transfers the charge generated by the photodiode 12.

As depicted in FIG. 3, in this example, the control electrode Tc is arranged on a region between the photodiode 12 and the drain 14 in the semiconductor substrate 2. That is, in this example, the control electrode Tc extends along the charge transfer channel Ch1. As is apparent from the control electrode Tc extending in a straight line shape in the X direction (see FIG. 2), in this case, the shape of the charge transfer channel Ch1 when seen from the direction normal to the semiconductor substrate 2 is basically a straight line shape. However, the shape of the charge transfer channel Ch1 is not restricted to this example, and a bend and/or curved portion may be included, for example.

An insulation layer 16 is arranged between the control electrode Tc and the semiconductor substrate 2. The insulation layer 16 is a silicon dioxide layer, for example. In this example, the power lines 21 and 22 are connected to the control electrode Tc, as described with reference to FIG. 2. The power lines 21 and 22 respectively supply a first voltage V1 and a second voltage V2 to the control electrode Tc. By controlling the potential of the control electrode Tc by way of the power lines 21 and 22, it is possible for an inversion layer to be formed in the region between the photodiode 12 and the drain 14. This inversion layer functions as a channel for transferring the signal charge generated by the photodiode 12 to the drain 14. That is, the charge transfer channel Ch1 may be an inversion layer formed in the semiconductor substrate 2. The first voltage V1 and the second voltage V2 may be supplied from the vertical scanning circuit 50 (see FIG. 1). In other words, the power lines 21 and 22 may be connected to the vertical scanning circuit 50.

By connecting the power lines 21 and 22 respectively in the vicinity of the end section of the photodiode 12 side of the control electrode Tc and in the vicinity of the end section of the drain 14 side, it is possible for mutually different voltages to be supplied to the end section of the photodiode 12 side of the control electrode Tc and the end section of the drain 14 side. By independently applying the mutually different first voltage V1 and second voltage V2 to both ends of the control electrode Tc by way of the power lines 21 and 22, it is possible to control the gradient of the potential in the charge transfer channel Ch1. The signal charge generated by the photodiode 12 is typically made to move toward the drain 14 by controlling the gradient of the potential in the charge transfer channel Ch1. It goes without saying that the first voltage V1 and the second voltage V2 may be a common voltage provided that the signal charge generated by the photodiode 12 can be made to move toward the drain 14.

As depicted in FIG. 4, similar to the control electrode Tc, the transfer gate electrode Tx can also be arranged on the insulation layer 16 formed on the semiconductor substrate 2. The gate control voltage Vt supplied to the transfer gate electrode Tx is set to a high level, and it is thereby possible for an inversion layer to be formed in the region between the charge transfer channel Ch1 and the charge accumulator Pa within the semiconductor substrate 2. By forming an inversion layer in the region between the charge transfer channel Ch1 and the charge accumulator Pa, it is possible to form a channel for charge movement between the charge transfer channel Ch1 and the charge accumulator Pa. In other words, a charge transfer channel Ch2 that branches from the charge transfer channel Ch1 is formed as the second charge transfer channel. By forming a channel between the charge transfer channel Ch1 and the charge accumulator Pa, at least a portion of the signal charge that moves within the charge transfer channel Ch1 can be transferred toward the charge accumulator Pa. That is, it can be said that the charge transfer channel Ch2 is a charge transfer channel for transferring at least a portion of the signal charge that moves within the charge transfer channel Ch1, toward the charge accumulator Pa. The charge accumulator Pa temporarily accumulates the signal charge transferred from the charge transfer channel Ch1 via the charge transfer channel Ch2.

If the gate control voltage Vt supplied to the transfer gate electrode Tx is set to a low level, the transfer of charge from the charge transfer channel Ch1 to the charge accumulator Pa is stopped. In this example, the region between the charge transfer channel Ch1 and the charge accumulator Pa within the semiconductor substrate 2, and the insulation layer 16 and the transfer gate electrode Tx on said region constitute a gate Gt that switches between transferring/not transferring charge to the charge accumulator Pa via the charge transfer channel Ch2. The opening and closing of this gate Gt is controlled using the gate control voltage Vt. In other words, in this example, the transfer of signal charge via the charge transfer channel Ch2 is electrically controlled.

The pixel cells 10A can have an interlayer insulation layer that covers the semiconductor substrate 2. Although not depicted in FIGS. 1 to 4, portions other than the photoelectric converter 12 of the pixel cells 10A are covered by a light-shielding layer. This light-shielding layer can be provided on the interlayer insulation layer arranged on the semiconductor substrate 2, for example. The light-shielding layer may be a wiring layer provided on a layer above the semiconductor substrate 2. For example, the control electrode Tc and/or the transfer gate electrode Tx may make up a portion of the light-shielding layer.

It is possible for the aforementioned pixel cells 10A to be manufactured using a known semiconductor process. It should be noted that from among the surfaces of the semiconductor substrate 2, it is advantageous if the surface of the side on which the insulation layer 16 is formed is not silicided. In particular, it is advantageous if the region corresponding to the charge transfer channel Ch1 and the region corresponding to the charge transfer channel Ch2 in the semiconductor substrate 2 (typically, a diffusion layer) are not silicided. By not siliciding the region corresponding to the charge transfer channel Ch1 and the region corresponding to the charge transfer channel Ch2 in the semiconductor substrate 2, it is possible to suppress the inclusion of noise caused by the presence of metal. Furthermore, variation in mobility caused by signal charge preferentially moving via silicide can be suppressed, and resistance in the channels can be made uniform.

(Signal Detection Operation in the Pixel Cells 10A)

Figure 5:
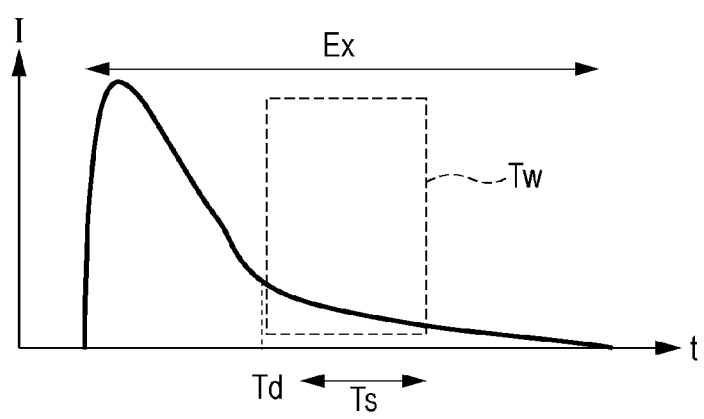
FIG. 5 is a drawing depicting an example of changes over time in the intensity of light incident upon a photodiode.
Figure 6:
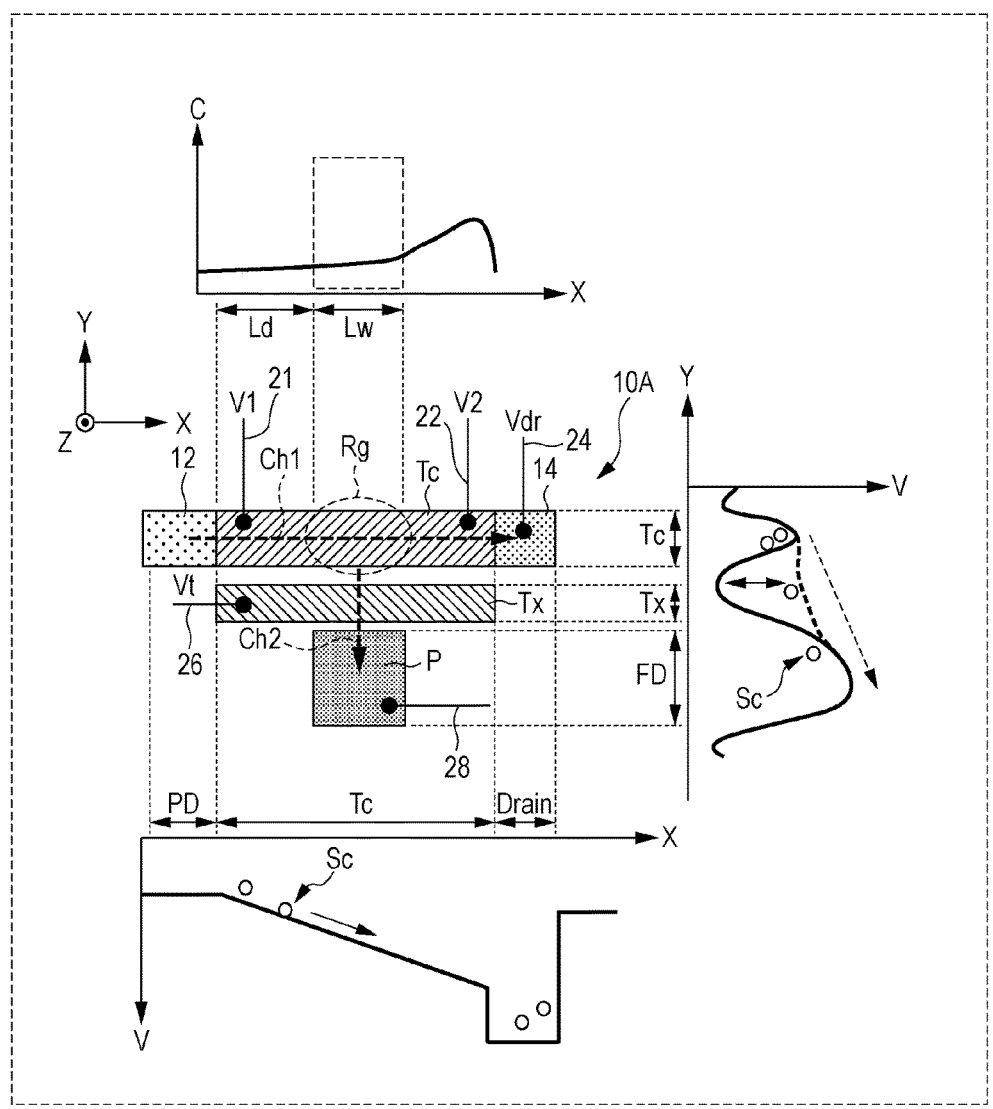
FIG. 6 is a drawing depicting a combination of a plan view of a pixel cell, an example of the distribution of signal charge within a charge transfer channel at a certain time, and an example of potential within a semiconductor substrate.

Next, an example of the signal detection operation in the pixel cells 10A will be described with reference to FIGS. 5 and 6. FIG. 5 depicts an example of changes over time in the intensity I of light that is incident upon the photodiode 12. In FIG. 5, the horizontal axis indicates time t, and both arrows Ex schematically indicate a light exposure period for the photodiode 12. FIG. 6 depicts a combination of a plan view of a pixel cell 10A, an example of the distribution of signal charge within the charge transfer channel Ch1 at a certain time, and an example of potential within the semiconductor substrate 2. The vertical axis of the graph depicted in the upper side of FIG. 6 represents an amount of charge C.

In FIG. 6, the charge transfer channel Ch1 that joins the photodiode 12 and the drain 14 is depicted by means of a thick dashed arrow. Furthermore, in FIG. 6, the charge transfer channel Ch2 is depicted by means of a thick dashed arrow extending in the Y direction. The charge transfer channels are also sometimes depicted by means of thick dashed arrows in other drawings. Hereinafter, an example in which electrons are used as signal charge will be described. It goes without saying that it is also possible for holes to be used as signal charge.

Prior to detecting light, a predetermined reset voltage is supplied to the charge accumulator P via a reset transistor, for example, thereby resetting the charge accumulator P. Furthermore, the voltage Vdr, which is relatively high, is applied to the drain 14 via the power line 24. In addition, the first voltage V1 is applied to the end section of the control electrode Tc near the photodiode 12, and the second voltage V2 is applied to the end section of the control electrode Tc near the drain 14, via the power lines 21 and 22, respectively. In this case, the first voltage V1 and the second voltage V2 are applied to the control electrode Tc in such a way as to satisfy the relationship Vdr>V2>V1.

The lower side in FIG. 6 depicts an example of change in potential in the X direction within the semiconductor substrate 2 in a state in which the voltage Vdr, the first voltage V1, and the second voltage V2 are applied. Furthermore, the right side in FIG. 6 depicts an example of change in potential in the Y direction within the semiconductor substrate 2. The white circles Sc in these graphs schematically represent signal charge. In the graph on the right side in FIG. 6, a solid line depicts the change in potential in the Y direction within the semiconductor substrate 2, in a state in which the voltage Vdr, the first voltage V1, and the second voltage V2 are applied.

Focusing on the change in energy of the signal charge (electrons in this case) in the X direction, in this example, the energy of the signal charge (electrons in this case) is highest in the vicinity of the photodiode 12 and decreases approaching the drain 14. Therefore, in a state in which the voltage Vdr, the first voltage V1, and the second voltage V2 are applied, the signal charge (electrons in this case) generated in the photodiode 12 moves toward the drain 14 through the charge transfer channel Ch1. The signal charge that reaches the drain 14 is discharged to outside of the pixel cells 10A via the power line 24. The state in which the voltage Vdr, the first voltage V1, and the second voltage V2 are applied can be said to be a state in which the photodiode 12 is reset.

In this case, it is assumed that light indicating changes over time such as those depicted in FIG. 5 is incident upon the photodiode 12. As mentioned above, in a state in which the voltage Vdr, the first voltage V1, and the second voltage V2 are applied, a potential gradient occurs in the charge transfer channel Ch1. Consequently, when signal charge is generated in the photodiode 12, the generated signal charge moves toward the drain 14.

In this case, the intensity I of the light incident upon the photodiode 12 changes over time, and therefore the amount of signal charge generated in the photodiode 12 also changes over time in accordance with the changes over time in the intensity I of the incident light. Therefore, the amount of signal charge that flows into the charge transfer channel Ch1 also indicates changes that correspond to the changes over time in the intensity I of the incident light. In other words, the amount of signal charge that passes through a certain point of the charge transfer channel Ch1 changes over time in accordance with the changes over time in the intensity I of the incident light. In other words, the amount of signal charge in the charge transfer channel Ch1 when a certain time has elapsed from the start of light being incident upon the photodiode 12 indicates a distribution that corresponds to changes over time in the intensity I of the incident light, as schematically depicted in the upper side of FIG. 6. When seen in a broad sense, this is because the movement distance in the charge transfer channel Ch1 of signal charge that has flowed into the charge transfer channel Ch1 at a certain time is longer than the movement distance of signal charge that has flowed into the charge transfer channel Ch1 at a time later than the aforementioned time.

It is assumed that, at a certain time after the start of exposure to light, the amount of signal charge within the charge transfer channel Ch1 indicates a distribution such as that of the graph schematically depicted in the upper side of FIG. 6. In this case, it is assumed that, at time Td, the gate control voltage Vt applied to the transfer gate electrode Tx has been set to a high level. By setting the gate control voltage Vt to a high level, a potential barrier between the charge transfer channel Ch1 and the charge accumulator P decreases, and the gate Gt (see FIG. 4) between the charge transfer channel Ch1 and the charge accumulator P enters an open state, as indicated by the dashed line in the center of the graph on the right side of FIG. 6.

By opening the gate Gt, the signal charge that is passing through the vicinity of a region Rg that overlaps with the transfer gate electrode Tx in the Y direction, among the signal charge passing through the charge transfer channel Ch1, is selectively transferred to the charge accumulator P via the charge transfer channel Ch2. Thereafter, after a time Ts (see FIG. 5) has elapsed from the time Td, the gate control voltage Vt is set to a low level and the gate Gt is closed. By closing the gate Gt, the transfer of signal charge to the charge accumulator P ends.

In this way, by arranging the charge accumulator P midway along the charge transfer channel Ch1 and controlling the opening and closing of the gate Gt between the charge transfer channel Ch1 and the charge accumulator P, it is possible for a portion of the signal charge moving along the charge transfer channel Ch1 to be selectively extracted to the charge accumulator P. As schematically depicted in FIG. 6, the amount of charge transferred to the charge accumulator P, among the signal charge in the charge transfer channel Ch1, is dependent upon the distance Ld from the end section of the photodiode 12 to the charge accumulator P and the width Lw of the charge accumulator P. The amount of charge transferred and accumulated in the charge accumulator P corresponds to the amount of charge generated in the photodiode 12 between the time Td and a time (Td+Ts). That is, the amount of charge transferred and accumulated in the charge accumulator P has information corresponding to the amount of light incident upon the photodiode 12 in the aforementioned time Ts, among the entire light exposure period for the photodiode 12 (the period indicated by the arrows Ex in FIG. 5). Consequently, if the charge accumulated in the charge accumulator P is read out, detection in a time window Tw (see FIG. 5) that starts at the time Td and corresponds to the time Ts is realized.

Next, with reference to FIGS. 7 and 8, an explanation will be given regarding signal detection in a configuration in which the pixel array PA has mixed therein two or more pixel cells that have mutually different distances Ld from the photodiode 12 to the charge accumulator P in the direction along the charge transfer channel Ch1. According to this kind of configuration, it becomes possible to detect signals in mutually different time windows.

Figure 7:
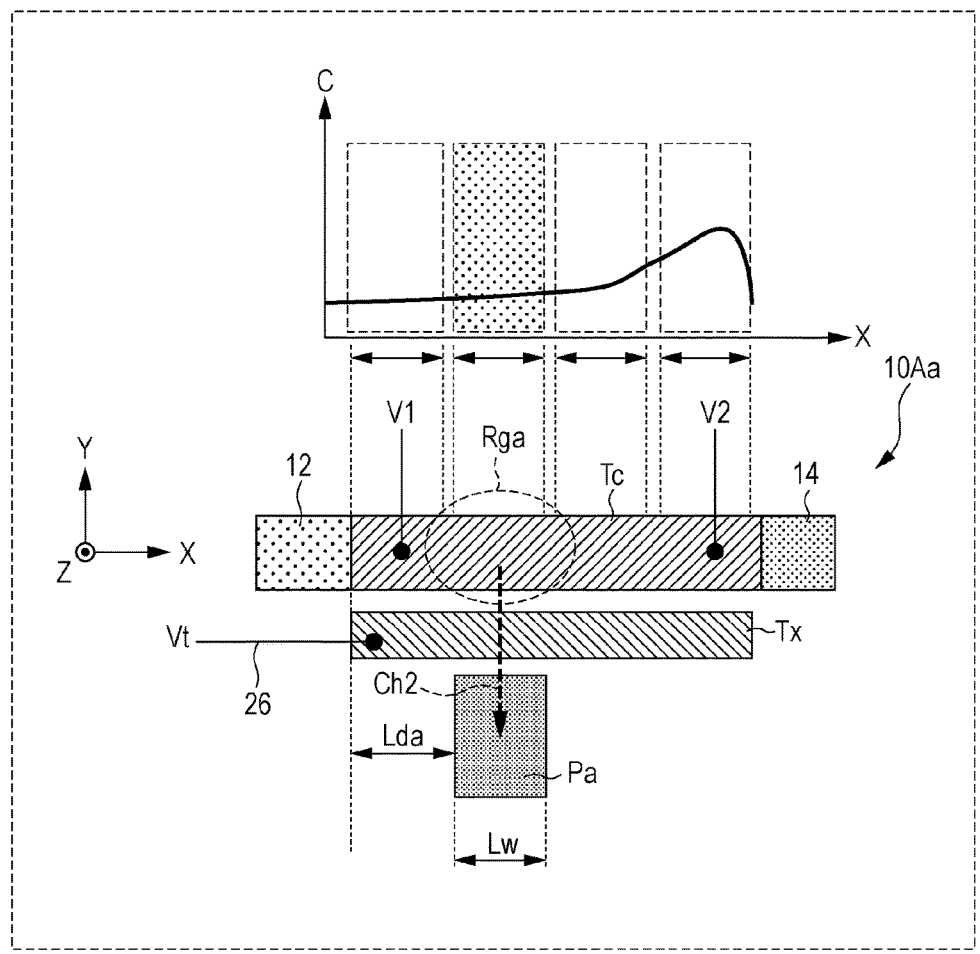
FIG. 7 is a drawing depicting a combination of a plan view of a pixel cell and an example of the distribution of signal charge within a charge transfer channel at a certain time.
Figure 8:
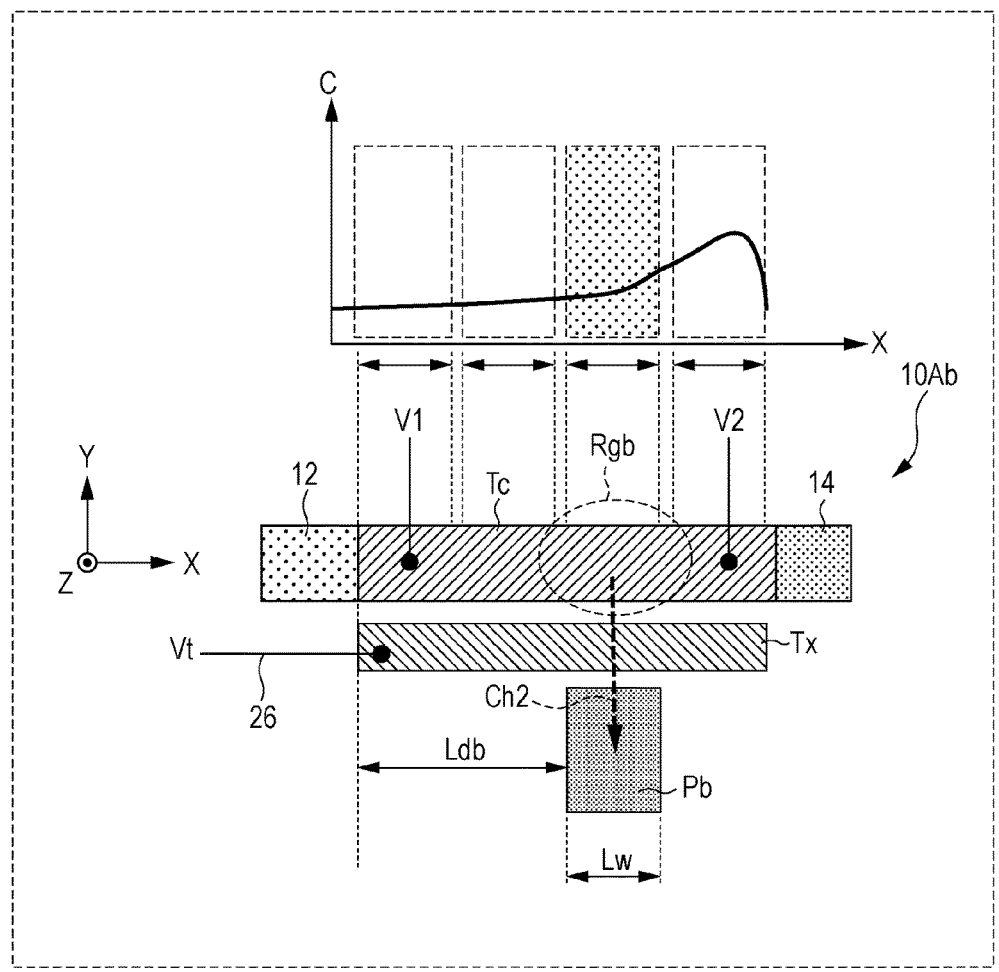
FIG. 8 is a drawing depicting a combination of a plan view of a pixel cell and an example of the distribution of signal charge within a charge transfer channel at a certain time.

FIG. 7 depicts a combination of a plan view of the pixel cell 10Aa and an example of the distribution of signal charge within the charge transfer channel Ch1 at a certain time. FIG. 8 depicts a combination of a plan view of the pixel cell 10Ab and an example of the distribution of signal charge within the charge transfer channel Ch1 at a certain time. In the configurations exemplified in FIGS. 7 and 8, the width of the charge accumulator Pa in the pixel cell 10Aa and the width of the charge accumulator Pb in the pixel cell 10Ab are common and are both Lw. In this case, the distance Ldb from the photodiode 12 to the charge accumulator Pb in the direction along the charge transfer channel Ch1 in the pixel cell 10Ab is more or less equal to a length obtained by adding Lw to the distance Lda from the photodiode 12 to the charge accumulator Pa in the direction along the charge transfer channel Ch1 in the pixel cell 10Aa.

It is assumed that the pixel cells 10Aa and 10Ab are two pixel cells arranged adjacent to each other in the pixel array PA, for example. The light exposure periods among the pixel cells 10A included in the pixel array PA are basically common. Consequently, it may be said that the intensity of light incident upon the pixel cell 10Aa and the pixel cell 10Ab and changes over time therein are the same. The graph depicted in the upper side of FIG. 7 depicts the distribution at a certain time of the signal charge within the charge transfer channel Ch1 when light exhibiting changes over time such as those depicted in FIG. 5 is incident upon the photodiode 12 of the pixel cell 10Aa. The graph depicted in the upper side of FIG. 8 depicts the distribution at a certain time of the signal charge within the charge transfer channel Ch1 when light exhibiting changes over time such as those depicted in FIG. 5 is incident upon the photodiode 12 of the pixel cell 10Ab.

As mentioned above, prior to light being detected, first, the charge accumulators Pa and Pb are reset. Thereafter, light exposure for the photodiode 12 of the pixel cell 10Aa and the photodiode 12 of the pixel cell 10Ab is started. The graphs in the upper side of each of FIGS. 7 and 8 schematically depict the distribution of signal charge within the charge transfer channel Ch1 when a certain time has elapsed from the start of light exposure. In this case, when the certain time has elapsed from the start of light exposure, the gate Gt in the pixel cell 10Aa and the gate Gt in the pixel cell 10Ab are opened by controlling the potential of the gate control lines 26. In addition, these gates Gt are closed when a predetermined time (typically of the order of several tens of picoseconds) has elapsed. By means of this kind of control, in the pixel cell 10Aa, signal charge located in the vicinity of a region Rga that overlaps with the charge accumulator Pa in the Y direction within the charge transfer channel Ch1 is transferred to the charge accumulator Pa via the charge transfer channel Ch2. Meanwhile, in the pixel cell 10Ab, signal charge located in the vicinity of a region Rgb that overlaps with the charge accumulator Pb in the Y direction within the charge transfer channel Ch1 is transferred to the charge accumulator Pb via the charge transfer channel Ch2.

In this case, Lda<Ldb, and the movement distance within the charge transfer channel Ch1 of charge that is generated in the photodiode 12 of the pixel cell 10Aa and transferred to the charge accumulator Pa is shorter than the movement distance in the charge transfer channel Ch1 of charge that is generated in the photodiode 12 of the pixel cell 10Ab and transferred to the charge accumulator Pb. In other words, after the certain time has elapsed from the start of light exposure, the signal charge located in the vicinity of the region Rga of the charge transfer channel Ch1 of the pixel cell 10Aa is charge that has been generated at a time later than that of the signal charge located in the vicinity of the region Rgb of the charge transfer channel Ch1 of the pixel cell 10Ab. That is, the transfer of signal charge to the charge accumulator Pb of the pixel cell 10Ab corresponds to detection in a time window that starts at a certain time, and the transfer of signal charge to the charge accumulator Pa of the pixel cell 10Aa corresponds to detection in a time window that starts at a certain time that is later than the aforementioned time.

In this way, pixel cells having mutually different charge transfer distances are arranged within the pixel array PA, and therefore detection in different time windows corresponding to the arrangement of the charge accumulator P can be realized among these pixel cells. As is clear from the aforementioned principle, according to the embodiment of the present disclosure, the arrangement of the charge accumulator P, in other words, the distance Ld from the photodiode 12 to the charge accumulator P in the direction along the charge transfer channel Ch1, is different among the plurality of pixel cells. It is thereby possible to easily change the starting point of the time window in detection. Furthermore, it is possible to adjust the width of the time window by means of the width Lw of the charge accumulator P, for example.

Not only may the charge transfer distance be differed between two pixel cells at arbitrary locations within the pixel array PA, but the charge transfer distance may also be monotonically increased or monotonically decreased among a series of a plurality of pixel cells arranged side-by-side in the row direction or the column direction. It is possible to reduce the effect of errors caused by signal delay or the like by not allowing the difference in charge transfer distance between mutually adjacent pixel cells to be extremely large.

The distance Ld from the photodiode 12 to the charge accumulator P in the direction along the charge transfer channel Ch1, for example, can be defined as the distance from the end section of the charge accumulator P side of the photodiode 12 to the end section of the photodiode 12 side of the charge accumulator P, in the direction in which the center of the photodiode 12 and the center of the drain 14 are joined (the X direction in this case), when seen from the direction normal to the semiconductor substrate 2. When the charge transfer channel Ch1 has a curved shape, for example, the distance Ld may be defined as the distance from the end section of the charge accumulator P side of the photodiode 12 to the end section of the photodiode 12 side of the charge accumulator P, along the center of the control electrode Tc, in a direction orthogonal to the direction in which one end of the control electrode Tc and the other end are joined. In other words, the distance Ld may be defined as the distance from the end section of the charge accumulator P side of the photodiode 12 to the end section of the photodiode 12 side of the charge accumulator P, along the center line of the control electrode Tc. Alternatively, the distance Ld may be defined as the distance from the end section of the charge accumulator P side of the photodiode 12 to the end section of the photodiode 12 side of the charge accumulator P, along the edge of the side near the charge accumulator P in the external shape of the control electrode Tc, when seen from the direction normal to semiconductor substrate 2.

In contrast to the conventional method in which all of the signal charge generated by a photodiode is transferred to a floating diffusion and read out, in the aforementioned exemplary operation, a portion of the signal charge moving within the charge transfer channel Ch1 toward the drain 14 is extracted and accumulated in the charge accumulator P. It is therefore possible to realize higher-speed detection compared to the conventional method in which all of the signal charge generated by a photodiode is transferred to a floating diffusion. In the embodiment of the present disclosure, the period for resetting the photodiode 12 is practically zero, and the period for accumulating signal charge is a portion of the light exposure period rather than the entirety thereof. Thus, it is possible to realize a higher-speed operation.

In addition, in the embodiment of the present disclosure, it is possible for the opening and closing of the gate Gt to be electrically controlled using the gate control voltage Vt, for example. By controlling the timing of the opening and closing of the gate Gt, it is possible for a portion of the signal charge moving within the charge transfer channel Ch1 toward the drain 14 to be extracted at an arbitrary start time and period, and accumulated in the charge accumulator P. In other words, it is easy for a portion of signal charge to be sampled in a desired time window. It is possible to adjust the width of the time window by adjusting the time at which the gate Gt opens. It should be noted that in the aforementioned example, the timing at which signal charge is transferred from the charge transfer channel Ch1 to the charge accumulator P via the charge transfer channel Ch2 is common among the plurality of pixel cells 10A. In this way, according to the embodiment of the present disclosure, it is possible for detection in different time windows to be executed collectively while not requiring complex control.

In the aforementioned exemplary operation, mutually different voltages are applied to both ends of the control electrode Tc. However, in the case where electrons are used as signal charge, it is possible for signal charge to move from the photodiode 12 toward the drain 14 if the potential of the drain 14 is higher than the potential of the photodiode 12, and therefore a common voltage may be applied to both ends of the control electrode Tc. However, by independently applying mutually different voltages to both ends of the control electrode Tc, it is possible to control the size of the potential gradient between the photodiode 12 and drain 14 in the charge transfer channel Ch1, via the insulation layer 16 under the control electrode Tc. Consequently, it is possible to electrically control the transfer speed of signal charge from the photodiode 12 to the drain 14. For example, by adjusting the potential gradient between the photodiode 12 and the drain 14, it is also possible to retrospectively adjust the starting point of a time window. Furthermore, for example, in the case where the aforementioned detection operation is to be repeatedly executed, the potential gradient in the charge transfer channel Ch1 may be altered each time the photodiode 12 is reset, and signal charge at different transfer speeds may be extracted to the charge accumulator P. Digital signals such as high-level and low-level digital signals or analog voltages of arbitrary magnitudes may be used as the first voltage V1 and the second voltage V2 that are applied to the control electrode Tc.

(Modified Examples of the Pixel Structure)

Figure 9:
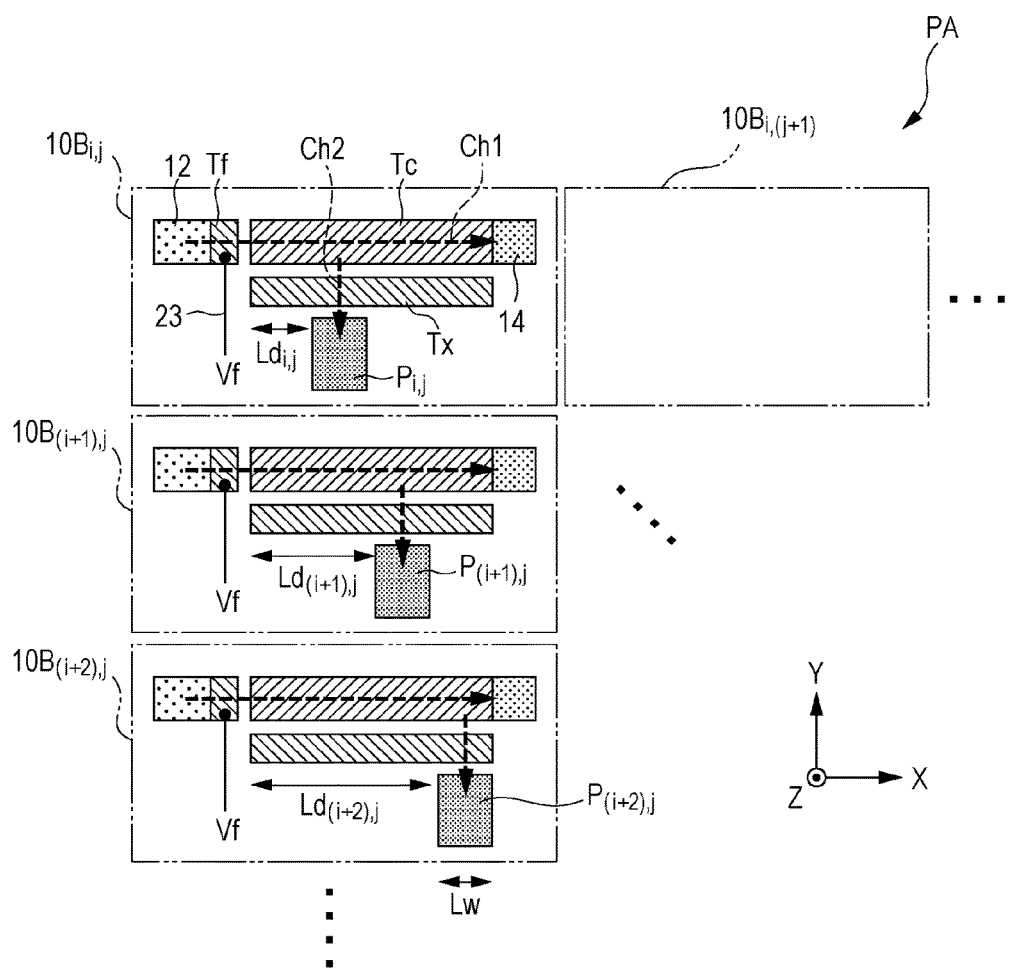
FIG. 9 is a plan view depicting a modified example of a pixel structure.

FIG. 9 depicts a modified example of the pixel structure. In the configuration exemplified in FIG. 9, the pixel array PA includes two or more pixel cells 10B having mutually different distances Ld from the photodiode 12 to the charge accumulator P. In this case, pixel cells $10B_{i,j}$, $10B_{(i+1),j}$, $10B_{(i+2),j}$, and $10B_{i,(j+1)}$ are depicted from among the pixel cells 10B. In this case, i and j are integers that are equal to or greater than zero, and the subscript index represents the arrangement in the pixel array PA (may also be referred to as coordinates in the pixel array PA).

In this example, the arrangement of charge accumulator $P_{i,j}$ in the pixel cell $10B_{i,j}$ in row i and column j, the arrangement of charge accumulator $P_{(i+1),j}$ in the pixel cell $10B_{(i+1),j}$ in row (i+1) and column j, and the arrangement of charge accumulator $P_{(i+2),j}$ in the pixel cell $10B_{(i+2),j}$ in row (i+2) and column j are different from each other. In the configuration exemplified in FIG. 9, the relationship $Ld_{i,j} < Ld_{(i+1),j} < Ld_{(i+2),j}$ is established among the distance $Ld_{i,j}$ in pixel cell $10B_{i,j}$, the distance $Ld_{(i+1),j}$ in pixel cell $10B_{(i+1),j}$, and the distance $Ld_{(i+2),j}$ in pixel cell $10B_{(i+2),j}$. For example, $Ld_{(i+1),j} = Ld_{i,j} + Lw$, and $Ld_{(i+2),j} = Ld_{i,j} + 2Lw$.

The pixel cells $10B_{i,j}$, $10B_{(i+1),j}$, and $10B_{(i+2),j}$ have a transfer gate electrode Tf arranged between the photodiode 12 and one end of the control electrode Tc. As depicted in the drawing, the distances from the end section of the control electrode Tc side of the transfer gate electrode Tf to the end section of the transfer gate electrode Tf side of the charge accumulator P in the X direction are mutually different among the pixel cells $10B_{i,j}$, $10B_{(i+1),j}$, and $10B_{(i+2),j}$.

A gate control line 23 that supplies a gate control voltage Vf is connected to each transfer gate electrode Tf. The gate control line 23 is connected to the vertical scanning circuit 50 (see FIG. 1), for example, and during operation of the imaging device 100, the potential of the gate control line 23 is controlled by the vertical scanning circuit 50. Typically, the transfer gate electrode Tf is arranged on the insulation layer 16 (see FIGS. 3 and 4) on the semiconductor substrate 2.

The transfer gate electrode Tf makes up a portion of the gate that switches between transferring/not transferring signal charge from the photodiode 12 to the charge transfer channel Ch1. If the gate control voltage Vf applied to the transfer gate electrode Tf is set to a high level, the gate between the photodiode 12 and the charge transfer channel Ch1 opens, and signal charge moves from the photodiode 12 toward the charge transfer channel Ch1. If the gate control voltage Vf is switched to a low level, the gate between the photodiode 12 and the charge transfer channel Ch1 closes, and the movement of signal charge from the photodiode 12 toward the charge transfer channel Ch1 is stopped. In other words, the amount of charge that flows to the charge transfer channel Ch1 can be adjusted by means of the voltage level of the gate control voltage Vf.

In this way, by arranging the transfer gate electrode Tf between the photodiode 12 and one end of the control electrode Tc, it is possible to electrically control the timing for starting and ending the transfer of signal charge from the photodiode 12 to the charge transfer channel Ch1. The transfer gate electrode Tf is small compared to the transfer gate electrode Tx, and therefore circuit load can be reduced compared to control with which the amount of charge transferred to the charge accumulator P is adjusted by means of the potential of the transfer gate electrode Tx. The effect of an increase in operation speed is obtained due to the reduction in load, and therefore temporal resolution can be improved.

Figure 10:
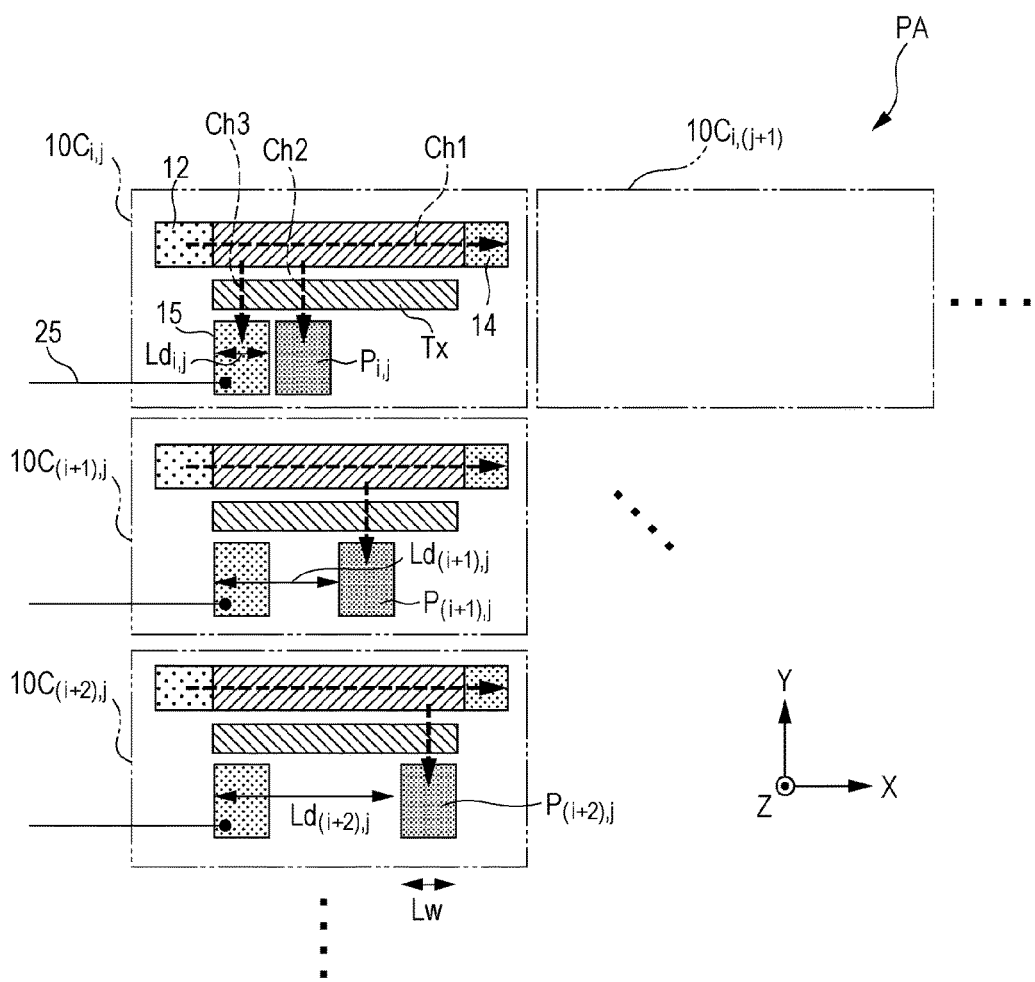
FIG. 10 is a plan view depicting another modified example of the pixel structure.

FIG. 10 depicts another modified example of the pixel structure. In the configuration exemplified in FIG. 10, the pixel array PA includes two or more pixel cells 100 having mutually different distances Ld from the photodiode 12 to the charge accumulator P. In the configuration exemplified in FIG. 10, the pixel cells $10C_{i,j}$, $10C_{(i+1),j}$, and $10C_{(i+2),j}$ have a second drain 15. The drain 15 may have the same configuration as that of the drain 14 located at an end of the charge transfer channel Ch1. The drain 15 may be an impurity region formed in the semiconductor substrate 2. The drain 15 of each pixel cell 100 is connected to a power line 25 connected to a power source that is not depicted, and during operation of the imaging device 100, a predetermined voltage is applied to the drain 15 via the power line 25.

Within each pixel cell 100, the drain 15 is arranged parallel to the charge accumulator P along the charge transfer channel Ch1. If the gate control voltage Vt applied to the transfer gate electrode Tx is set to a high level, the gate between the charge transfer channel Ch1 and the charge accumulator P opens, and, among the signal charge passing through the charge transfer channel Ch1, the signal charge passing through the vicinity of a region that overlaps with the charge accumulator P in the Y direction is transferred to the charge accumulator P via the charge transfer channel Ch2. At such time, the gate between the charge transfer channel Ch1 and the drain 15 also opens, and, among the signal charge passing through the charge transfer channel Ch1, the signal charge passing through the vicinity of a region that overlaps with the drain 15 in the Y direction is transferred to the drain via a charge transfer channel Ch3 that branches from the charge transfer channel Ch1. In each pixel cell 100, the ratio between the width of the charge accumulator P and the width of the drain 15 in the direction along the charge transfer channel Ch1 can be arbitrarily set.

As schematically depicted in FIG. 10, the drain 15 is arranged closer to the photodiode 12 than the charge accumulator P. Consequently, the transfer to the drain 15 of charge moving from the photodiode 12 toward the drain 14 means that signal charge generated at a certain time and thereafter is recovered by the drain 15. In other words, by providing the second drain 15 within the pixel cells 10C, it is possible to suppress inclusion into the charge accumulator P of signal charge generated at a certain time and thereafter. According to this kind of configuration, power consumption can be reduced since it is not necessary for the gate control voltage Vt to be switched to a low level immediately after being set to a high level. The gate control voltage Vt may be maintained at a high level without being set to a low level. It should be noted that the drain 15 can also be used as a charge accumulator.

Figure 11:
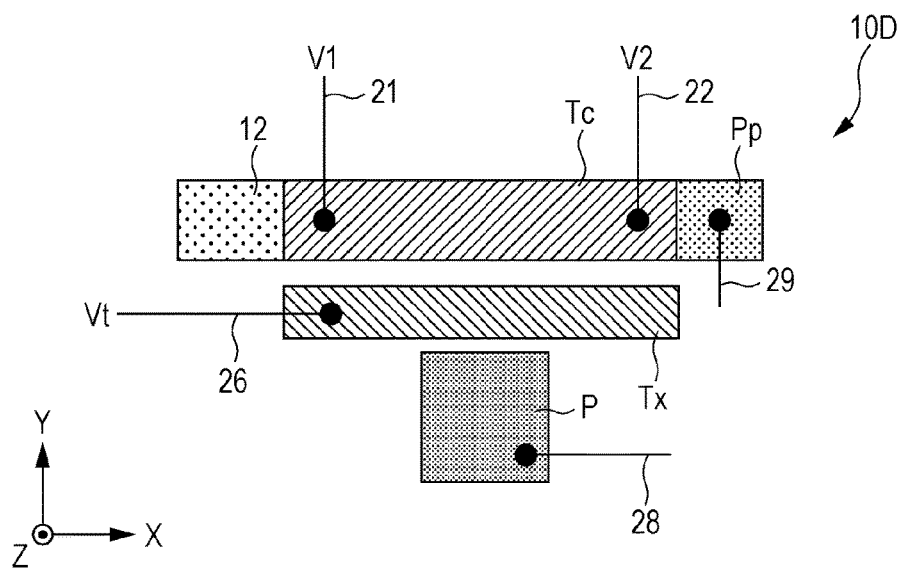
FIG. 11 is a plan view depicting yet another modified example of the pixel structure.

FIG. 11 depicts another modified example of the pixel structure. As in a pixel cell 10D depicted in FIG. 11, instead of the drain 14, a second charge accumulator Pp may be arranged at an end of the charge transfer channel Ch1.

The second charge accumulator Pp accumulates at least a portion of the charge transferred via the charge transfer channel Ch1. The potential of the charge accumulator Pp is fixed during the accumulation of signal charge in the charge accumulator Pp. In the configuration exemplified in FIG. 11, a read-out line 29 is connected to the charge accumulator Pp. This read-out line 29 can be connected to a signal detection circuit that is independent from the signal detection circuit connected to the charge accumulator P via the read-out line 28.

According to a configuration such as that depicted in FIG. 11 in which charge accumulators are arranged at an end of the charge transfer channel Ch1 and in a section other than said end, it is possible for charge to be distributed at an arbitrary ratio between the two charge accumulators (charge accumulators P and Pp) by controlling the open period for the gate provided between the charge accumulator P and the charge transfer channel Ch1.

(Example of the Arrangement of Pixel Cells)

Hereinafter, an example of the arrangement of pixel cells will be described with reference to FIGS. 12 to 15.

Figure 12:
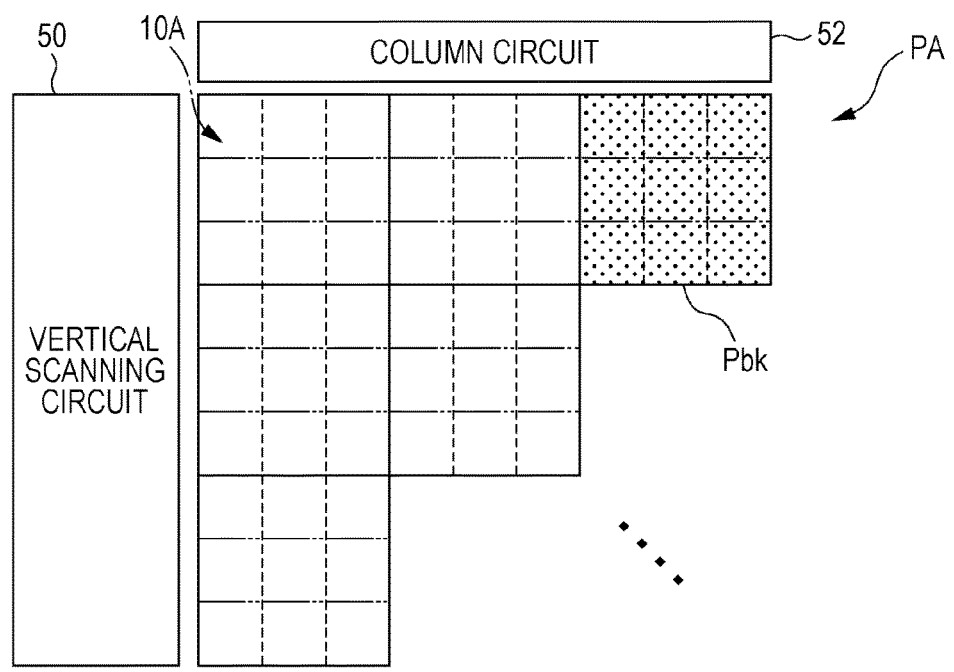
FIG. 12 is a plan view depicting an example of an arrangement of pixel cells.

FIG. 12 depicts an example of the arrangement of the pixel cells 10A. In the configuration exemplified in FIG. 12, the pixel array PA has an arrangement of pixel blocks Pbk that include a plurality of the pixel cells 10A. In this example, an imaging region is formed by a plurality of the pixel blocks Pbk being arranged in a plurality of rows and columns. As schematically depicted in FIG. 12, in this case, each pixel block Pbk includes nine pixel cells 10A arranged in a 3×3 matrix form.

Figure 13:
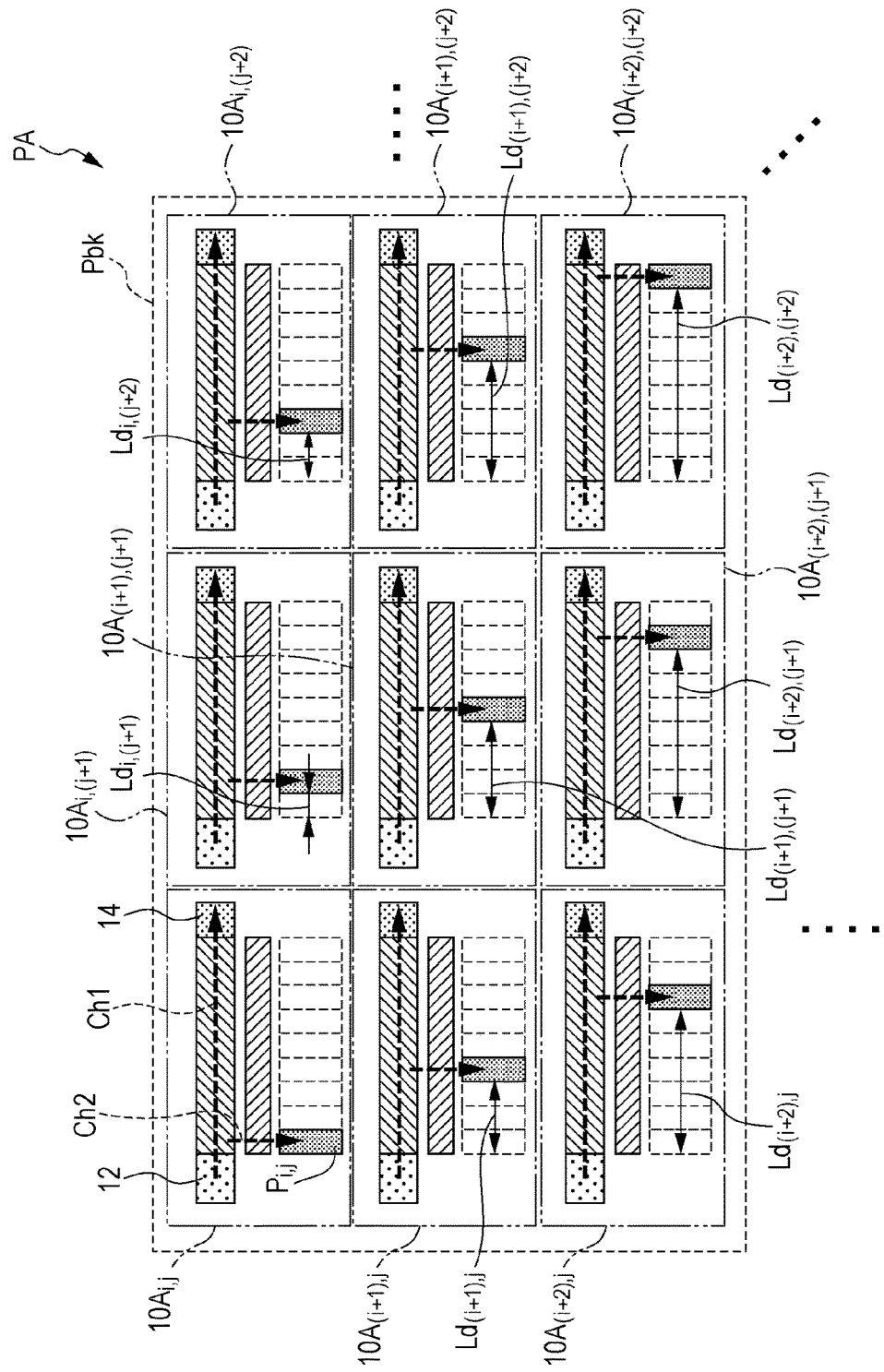
FIG. 13 is a plan view depicting one pixel block taken out from the pixel array depicted in FIG. 12.
Figure 14:
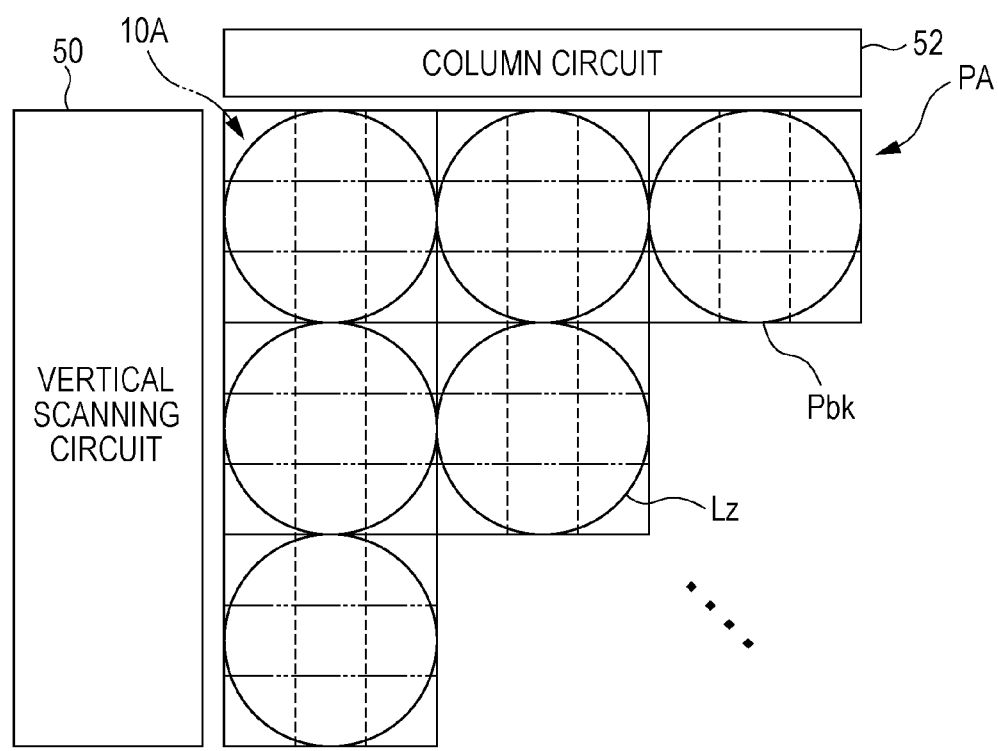
FIG. 14 is a plan view depicting an example of a pixel array that has a microlens arranged in each pixel block.

FIG. 13 depicts one pixel block Pbk taken out from the pixel array PA depicted in FIG. 12. In this example, the distances from the photodiode 12 to the charge accumulator P along the charge transfer channel Ch1 in the nine pixel cells 10A included in the pixel block Pbk are different from each other. In this example, the pixel block Pbk includes the pixel cells $10A_{i,j}$, $10A_{i,(j+1)}$, $10A_{i,(j+2)}$, $10A_{(i+1),j}$, $10A_{(i+1),(j+1)}$, $10A_{(i+1),(j+2)}$, $10A_{(i+2),j}$, $10A_{(i+2),(j+1)}$, and $10A_{(i+2),(j+2)}$. As schematically depicted in FIG. 13, in this case, the distance $Ld_{i,j}$ from the photoelectric converter 12 to the accumulator P in the pixel cell $10A_{i,j}$ is substantially zero, and the distance from the photoelectric converter 12 to the accumulator P in the nine pixel cells 10A included in the pixel block Pbk successively increases by the width Lw of the charge accumulator P in the aforementioned order. For example, the distance $Ld_{(i+2),(j+2)}$ from the photoelectric converter 12 to the accumulator P 14 in the pixel cell $10A_{(i+2),(j+2)}$ satisfies the relationship $Ld_{(i+2),(j+2)} = Ld_{i,j} + 8 Lw$. In this example, in the case where the light exposure period is common among the nine pixel cells 10A, a signal acquired by the pixel cell $10A_{(i+2),(j+2)}$ corresponds to the amount of signal charge generated in the initial stage of the light exposure period, while a signal acquired by the pixel cell $10A_{i,j}$ corresponds to the amount of signal charge generated in the last stage of the light exposure period. In other words, the time windows in each of the pixel cells 10A within the pixel block Pbk are different from each other.

In the example depicted in FIG. 12, the other pixel blocks Pbk also have the same configuration as that of the pixel block Pbk depicted in FIG. 13. That is, if m and n are taken as integers that are equal to or greater than 0, for example, the time window for detection in pixel cell $10A_{(i+2),\ (j+2)}$ and the time window for detection in pixel cell $10A_{(i+2+3n),\ (j+2+3m)}$, which is in a location shifted by 3m in the row direction and 3n in the column direction in the pixel array PA from said pixel cell $10A_{(i+2),\ (j+2)}$, are common. By selectively acquiring signals from the pixel cells 10A having common time windows, image signals for constructing an image corresponding to a certain time window are obtained. For example, if the output of the pixel cell 10A in the location having the coordinates (i+2+3n, j+2+3m) is collected, it is possible to construct an image corresponding to the time window of the initial stage of the light exposure period. Likewise, if the output of the pixel cell 10A in the location having the coordinates (i+2+3n, j+1+3m) is selectively acquired, it is possible to construct an image corresponding to the next time window.

Consequently, according to this kind of arrangement of the pixel cells 10A, it is possible for detection in nine mutually different time windows to be executed collectively with a single exposure. In other words, it is possible for image data for nine images corresponding to nine mutually different time windows to be acquired at high speed. As exemplified in FIG. 14, in each pixel block Pbk, there may be arranged a microlens Lz that opposes the plurality of pixel cells 10A within the pixel block Pbk. By arranging a microlens Lz in each pixel block Pbk, an application similar to that of a compound-eye camera becomes possible.

Figure 15:
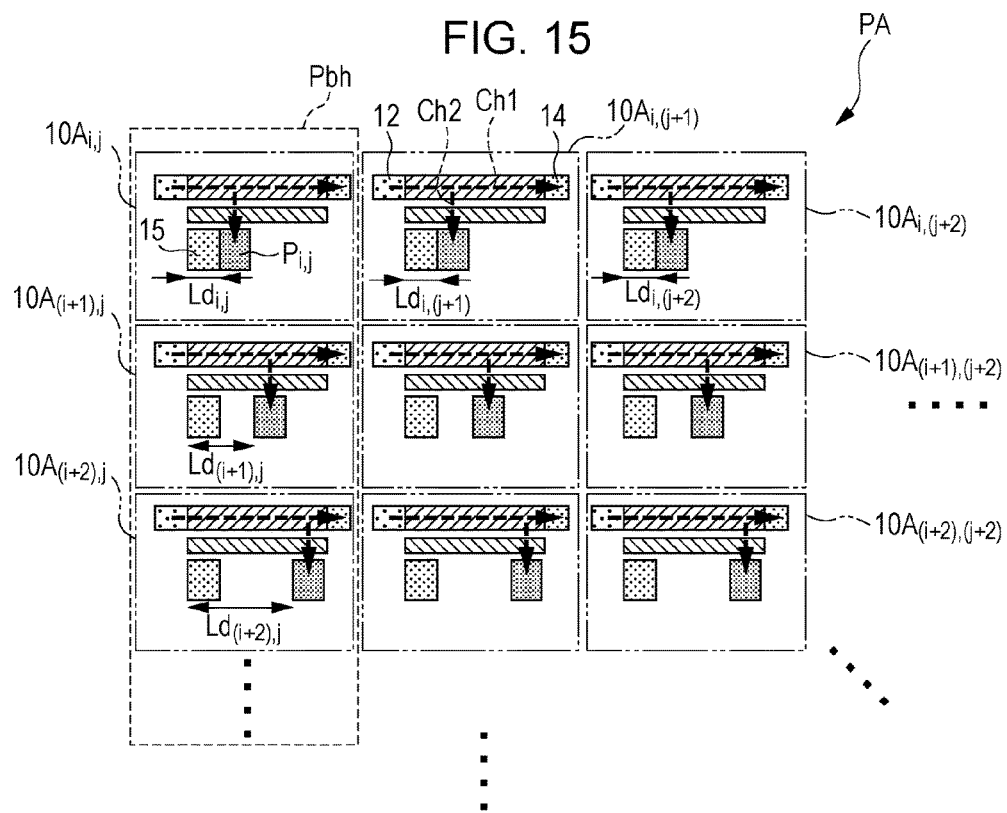
FIG. 15 is a plan view depicting another example of the pixel cell arrangement.

FIG. 15 depicts another example of the pixel cell arrangement. In the configuration exemplified in FIG. 15, the distances from the photodiode 12 to the charge accumulator P along the charge transfer channel Ch1 are different from each other among the pixel cells 10A belonging to the same column. For example, in this case, the relationship $Ld_{i,\ j} < Ld_{(i+1),\ j} < Ld_{(i+2),\ j}$ is established. Meanwhile, the distances from the photodiode 12 to the charge accumulator P along the charge transfer channel Ch1 are common among the pixel cells 10A belonging to the same row. In other words, in this case, the relationship $Ld_{i,\ j} = Ld_{i,\ (j+1)} = Ld_{i,\ (j+2)}$ is established. In the example depicted in FIG. 15, it can be said that the pixel array PA includes an arrangement of pixel blocks Pbh having arranged therein in the column direction a plurality of pixel cells 10A having mutually different distances Ld from the photodiode 12 to the charge accumulator P along the charge transfer channel Ch1. The pixel blocks Pbh are arranged in the row direction in the pixel array PA.

Focusing on column j, for example, the relationship $Ld_{i,j} < Ld_{(i+1),j} < Ld_{(i+2),j}$ is established, and therefore a signal corresponding to signal charge generated at a certain time is obtained from the pixel cell $10A_{(i+2),\ j}$, and a signal corresponding to signal charge generated at a time later than the aforementioned time is obtained from the pixel cell $10A_{(i+1),\ j}$. A signal corresponding to signal charge generated at an even later time is obtained from the pixel cell $10A_{i,\ j}$. In this way, the charge transfer distance (the distance from the photodiode 12 to the charge accumulator P) may be mutually differed in each row of the plurality of pixel cells 10A. In this example, the distances Ld from the photodiode 12 to the charge accumulator P along the charge transfer channel Ch1 are different in row units. In other words, the pixel cells 10A having common time windows are arranged in the row direction. Similar to a rolling shutter in a general digital camera, each row in the pixel array PA can be used as a line sensor by selectively acquiring the output from the pixel cells 10A in the same row. According to this kind of configuration, it is possible for data of a plurality of rows to be acquired collectively with a single exposure without moving the sensor itself in the column direction. Viewed from another angle, it can also be said that it is possible to obtain an effect similar to when a so-called rolling shutter has been executed at high speed, with a single exposure.

Second Embodiment

Figure 16:
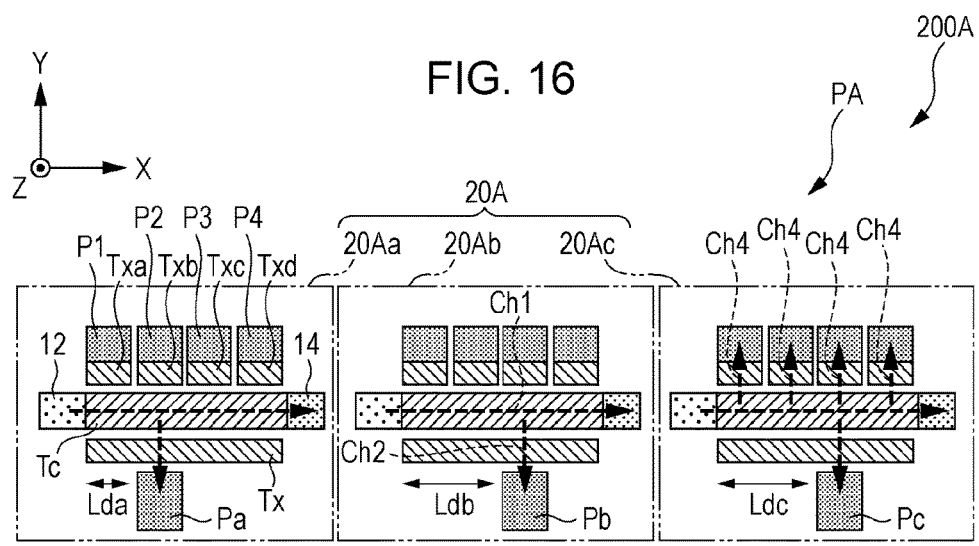
FIG. 16 is a schematic plan view depicting a pixel array in an imaging device according to a second embodiment of the present disclosure.

FIG. 16 depicts a pixel array PA in an imaging device according to a second embodiment of the present disclosure. The pixel array PA in an imaging device 200A depicted in FIG. 16 includes an arrangement of a plurality of pixel cells 20A. In FIG. 16, the three pixel cells of pixel cell 20Aa, pixel cell 20Ab, and pixel cell 20Ac are depicted in a representative manner from among the plurality of pixel cells 20A. Similar to the imaging device 100 according to the first embodiment, the imaging device 200A has, in the pixel array PA, two or more pixel cells having mutually different charge transfer distances from a photoelectric converter 12 to a charge accumulator P. In the configuration exemplified in FIG. 16, distances Ld when measured in a direction along a charge transfer channel Ch1 from the photodiode 12 to the charge accumulator P are different from each other among the pixel cell 20Aa, the pixel cell 20Ab, and the pixel cell 20Ac. In this case, a distance Ldb from the photodiode 12 to a charge accumulator Pb in the pixel cell 20Ab is approximately two times a distance Lda from the photodiode 12 to a charge accumulator Pa in the pixel cell 20Aa. A distance Ldc from the photodiode 12 to a charge accumulator Pc in the pixel cell 20Ac is approximately three times the distance Lda from the photodiode 12 to the charge accumulator Pa in the pixel cell 20Aa.

Each pixel cell 20Aa, pixel cell 20Ab, and pixel cell 20Ac additionally has four charge accumulators P1 to P4 arranged along the charge transfer channel Ch1, on the opposite side of the charge transfer channel Ch1 to the charge accumulator P. A transfer gate electrode Txa is arranged between the charge transfer channel Ch1 and the charge accumulator P1. Likewise, transfer gate electrodes Txb, Txc, and Txd are arranged respectively between the charge transfer channel Ch1 and the charge accumulator P2, between the charge transfer channel Ch1 and the charge accumulator P3, and between the charge transfer channel Ch1 and the charge accumulator P4. Typically, the transfer gate electrodes Txa to Txd are arranged on an insulation layer 16 (see FIGS. 3 and 4) on a semiconductor substrate 2, similar to the transfer gate electrode Tx.

As schematically depicted in FIG. 16, each pixel cell 20Aa, pixel cell 20Ab, and pixel cell 20Ac includes a plurality of charge transfer channels Ch4 that branch midway along the charge transfer channel Ch1. The charge accumulators P1 to P4 are located at ends of the charge transfer channels Ch4. Each of the aforementioned transfer gate electrodes Txa to Txd makes up part of a gate that switches between transferring/not transferring charge to the charge accumulators P1 to P4 via the corresponding charge transfer channel Ch4.

Figure 17:
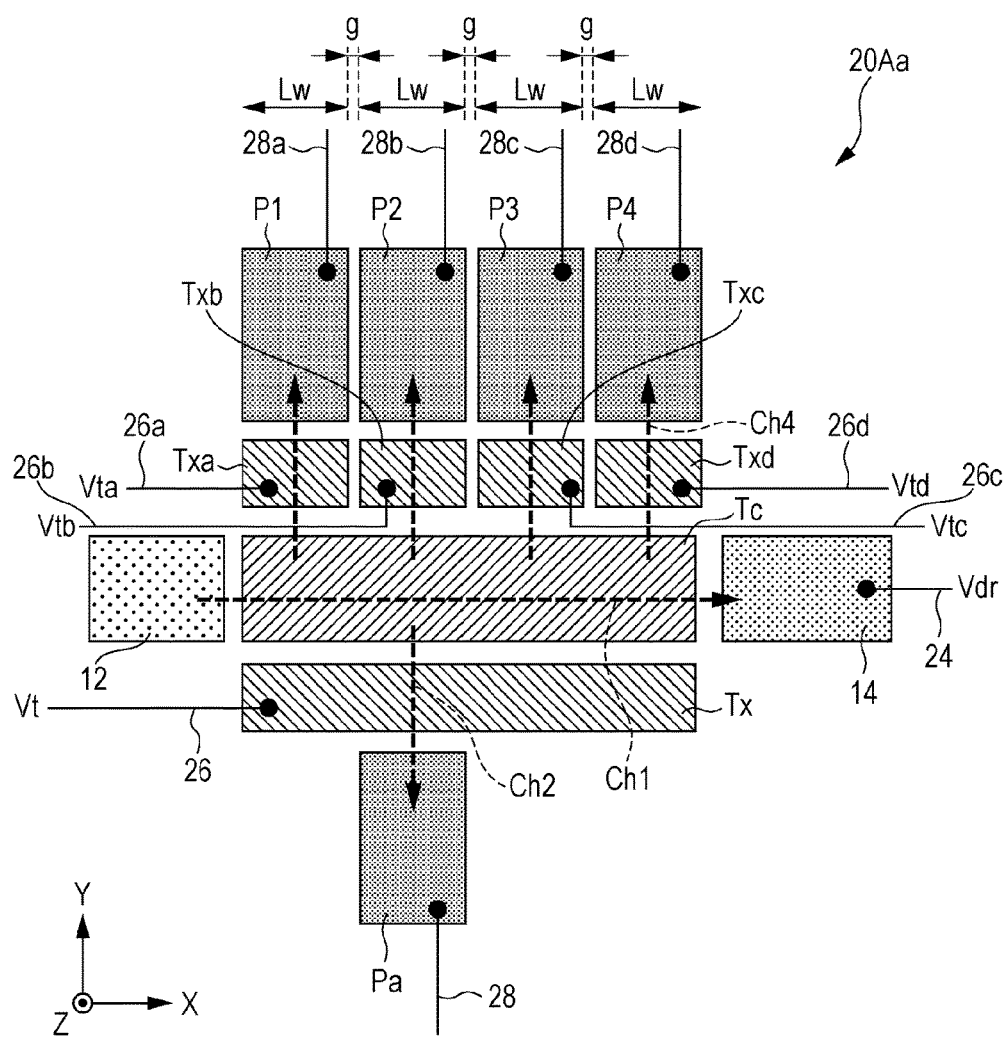
FIG. 17 is a plan view depicting an enlarged view of a pixel cell depicted in FIG. 16.

FIG. 17 depicts an enlarged view of the pixel cell 20Aa depicted in FIG. 16. In the configuration exemplified in FIG. 17, each of the charge accumulators P1 to P4 has a common width Lw, and the charge accumulators P1 to P4 are arranged separated from each other by an interval g. In this case, the four charge accumulators P1 to P4 are arranged on the opposite side of the charge transfer channel Ch1 to the charge accumulator Pa. However, the number of charge accumulators that are arranged on the opposite side of the charge transfer channel Ch1 to the charge accumulator P, and the widths and intervals thereof are not restricted to this example and can be arbitrarily set. For example, the number of charge accumulators of each pixel cell 20A is not restricted to five, and the widths or intervals among the plurality of charge accumulators may be different. For example, the ratio between lengths (widths) in the direction along the charge transfer channel Ch1 among the charge accumulators P1 to P4 may be a ratio corresponding to a ratio at which it is desired for temporal resolution to be implemented.

Gate control lines 26a to 26d are respectively connected to the transfer gate electrodes Txa to Txd. The gate control lines 26a to 26d respectively supply gate control voltages Vta to Vtd. The gate control lines 26a to 26d, for example, are connected to a vertical scanning circuit 50 (see FIG. 1). For example, the opening and closing of the gate between the charge transfer channel Ch1 and the charge accumulator P1 is controlled by means of the potential of the gate control line 26a. By setting the gate control voltage Vta to a high level, it is possible for a portion of the signal charge moving within the charge transfer channel Ch1 to be selectively extracted to the charge accumulator P1. In this example, the pixel cell 20Aa, corresponding to having the four charge accumulators P1 to P4, has four charge transfer channels Ch4 that transfer charge from the charge transfer channel Ch1 toward the charge accumulators P1 to P4.

Typically, the charge accumulators P1 to P4 have substantially the same configuration as the charge accumulator Pa, and function as storages that temporarily accumulate signal charge. In this example, read-out lines 28a to 28d are respectively connected to the charge accumulators P1 to P4, and each read-out line 28a to 28d has a non-depicted signal detection circuit including an amplification transistor or the like connected thereto. Consequently, it is possible for signals corresponding to the amounts of charge accumulated in the charge accumulators P1 to P4 to be individually read out via the read-out lines 28a to 28d. It should be noted that the charge accumulators P1 to P4 may be connected to a reset voltage line that supplies a reset voltage.

(Signal Detection Operation in Pixel Cells 20A)

Figure 18:
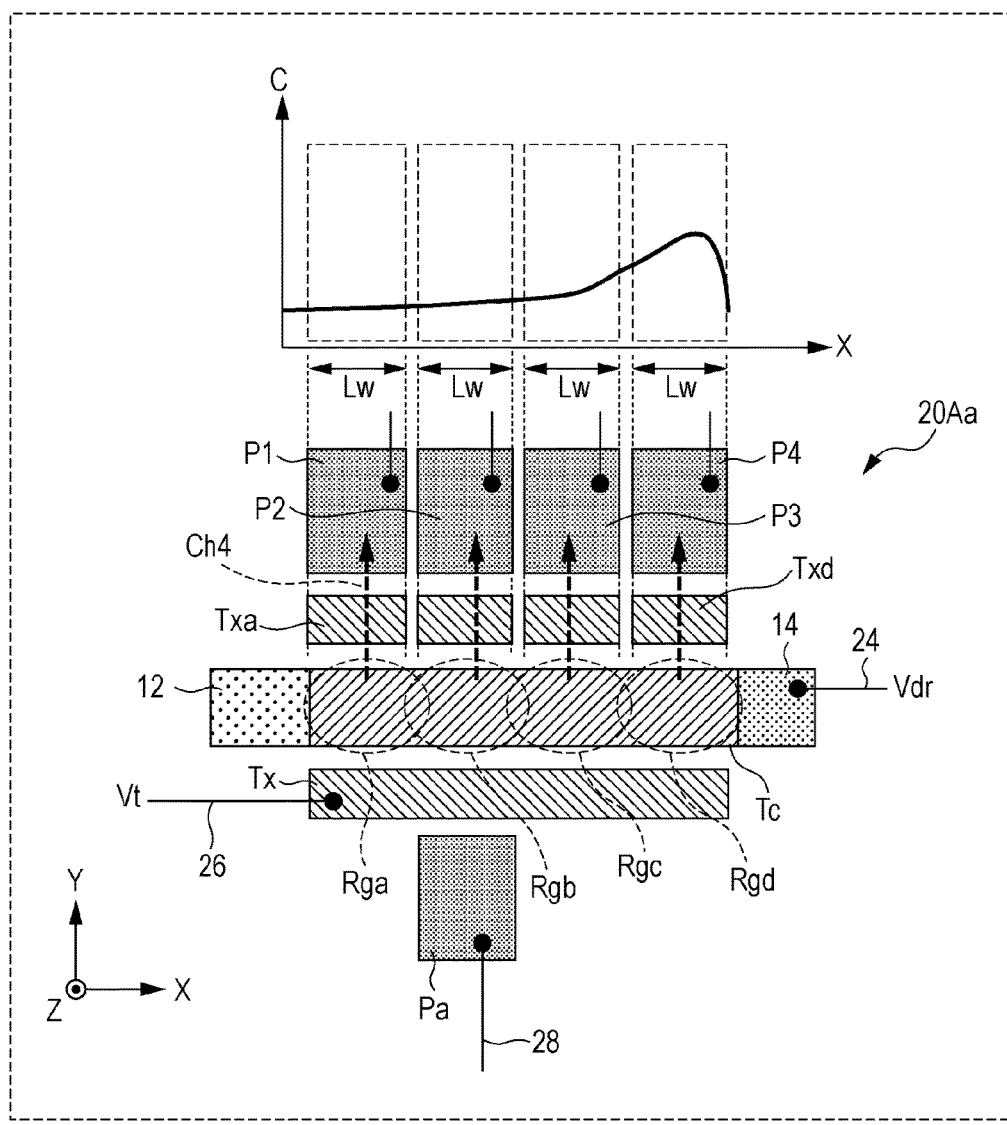
FIG. 18 is a drawing depicting a combination of a plan view of the pixel cell and an example of the distribution of signal charge within a charge transfer channel at a certain time.

Next, an example of the signal detection operation in the pixel cells 20A will be described with reference to FIG. 18. FIG. 18 depicts a combination of a plan view of the pixel cell 20Aa and an example of the distribution of signal charge within the charge transfer channel Ch1 at a certain time. By arranging the four charge accumulators P1 to P4 along the charge transfer channel Ch1, detection in four consecutive time windows (four phases) is possible, as described hereinafter.

Prior to detecting light, the charge in each of the charge accumulators P1 to P4 is reset. Typically, the charge in the charge accumulator Pa is also reset. At this point in time, a first voltage V1 and a second voltage V2 applied to a control electrode Tc, and the gate control voltages Vt and Vta to Vtd are all low level. Next, a voltage Vdr, the first voltage V1, and the second voltage V2 satisfying the relationship of Vdr>V2>V1 are applied to a drain 14 and the control electrode Tc, and a potential gradient is formed within the charge transfer channel Ch1. In this state, the input of light onto the photodiode 12 is started. The signal charge generated in the photodiode 12 moves within the charge transfer channel Ch1 toward the drain 14.

The amount of signal charge within the charge transfer channel Ch1 when a certain time has elapsed from the start of light being incident upon the photodiode 12 indicates a certain distribution as depicted in the upper side of FIG. 18.

In this case, when the gate control voltages Vta to Vtd that are applied to the transfer gate electrodes Txa to Txd are simultaneously set to a high level, potential barriers between the charge transfer channel Ch1 and each of the charge accumulators P1 to P4 decrease, and gates between the charge transfer channel Ch1 and each of the charge accumulators P1 to P4 enter an open state.

Due to the gates being open, the signal charge moving within the charge transfer channel Ch1 is transferred to the charge accumulators P1 to P4 via the charge transfer channels Ch4. At such time, the signal charge moving within the charge transfer channel Ch1 is transferred to any of the charge accumulators P1 to P4. Which of the charge accumulators P1 to P4 to which the signal charge moving within the charge transfer channel Ch1 is transferred differs according to the travel distance of the signal charge of interest when the gates are open. For example, signal charge located in the vicinity of a region Rga that overlaps with the charge accumulator P1 in the Y direction is transferred to the charge accumulator P1. Signal charge located in the vicinity of a region Rgb that overlaps with the charge accumulator P2 in the Y direction is transferred to the charge accumulator P2. Signal charge located in the vicinity of a region Rgc that overlaps with the charge accumulator P3 in the Y direction is transferred to the charge accumulator P3. Signal charge located in the vicinity of a region Rgd that overlaps with the charge accumulator P4 in the Y direction is transferred to the charge accumulator P4.

In this way, by arranging the plurality of charge accumulators P1 to P4 along to the charge transfer channel Ch1, it is possible for signal charge moving within the charge transfer channel Ch1 to be distributed between the charge accumulators P1 to P4 in accordance with movement distance at the point in time when the gates are open. In other words, it is possible for signal charge generated by the input of light to be detected in time windows corresponding to the arrangement of the charge accumulators P1 to P4 and the widths therein. By arranging the plurality of charge accumulators P1 to P4 along the charge transfer channel Ch1 in this way, it is possible for detection in time windows that start at different times to be executed collectively. It should be noted that the transfer gate electrodes Txa to Txd may be a single electrode.

For example, 100 ps is required for signal charge (electrons, for example) to move along a 4 μm-long charge transfer channel when an electric field of an intensity such that saturation velocity is 0.04 μm/ps is applied to the 4 μm-long charge transfer channel. Consequently, in a configuration in which signal charge is to be transferred directly to a charge accumulator via a 4 μm-long charge transfer channel, 100 ps is required even only for transferring signal charge. In contrast, according to a configuration in which the plurality of charge accumulators P1 to P4 are arranged along the charge transfer channel Ch1 having the drain 14 arranged at an end thereof, and electrons moving within the charge transfer channel Ch1 are distributed between the plurality of charge accumulators P1 to P4, as depicted in FIGS. 16 to 18, it is possible to improve temporal resolution. For example, if four charge accumulators are arranged along a 4 μm-long charge transfer channel, temporal resolution of approximately 25 ps can be realized even with the same electric field intensity.

By distributing signal charge generated by a photoelectric converter between a plurality of charge accumulators in accordance with the movement distance of the signal charge while the signal charge is being transferred to a drain, it is possible to improve temporal resolution in detection without the saturation velocity of the signal charge (electrons, for example) being restricted. If a configuration such as the aforementioned example, in which signal charge is distributed between the plurality of charge accumulators P1 to P4 in accordance with movement distance in the charge transfer channel Ch1, is applied to imaging that uses near-infrared light, for example, it is possible to obtain information regarding the depth direction in a measurement subject. At such time, it is possible for the signal-to-noise ratio to be improved by repeating the cycle of the input of an optical pulse and the transfer and accumulation of signal charge described with reference to FIG. 18, and integrating the amounts of charge in the charge accumulators P1 to P4. The opening of the gates provided in the charge transfer channels Ch4 for transferring charge to the charge accumulators P1 to P4 may be executed at a predetermined timing for every irradiation of an optical pulse.

It should be noted that, needless to say, an operation similar to that of the first embodiment is possible if the gate control voltage Vt that is applied to the transfer gate electrode Tx is set to a high level, instead of setting the gate control voltages Vta to Vtd that are applied to the transfer gate electrodes Txa to Txd to a high level simultaneously. According to a configuration in which the charge accumulators P1 to P4 are additionally arranged on the opposite side of the charge transfer channel Ch1 to the charge accumulator P, as exemplified in FIG. 17, by controlling the gate control voltage Vt and the gate control voltages Vta to Vtd, it is possible for the transfer destination of signal charge moving within the charge transfer channel Ch1 to be selected from among the charge accumulator P and the charge accumulators P1 to P4.

Owing to the transfer of signal charge to the charge accumulators P1 to P4, detection in a plurality of time windows can be executed simultaneously for each pixel cell 20A. However, it is possible that a leak between two mutually adjacent charge accumulators from among the charge accumulators P1 to P4 may occur. Then again, owing to the transfer of signal charge to the charge accumulator P, the number of charge accumulators P used for detection per pixel cell 20A is one, and therefore signal charge can be sufficiently isolated from that of other pixel cells 20A.

According to the second embodiment, it is possible to easily switch the charge accumulator to be used, and therefore it is possible to flexibly switch the transfer destination for signal charge in accordance with which is to be prioritized from among collective detection in a plurality of time windows and isolation of signal charge among the pixel cells 20A. It should be noted that holes may be used instead of electrons as signal charge. By using holes having relatively low mobility, in the case where signal charge is to be transferred to the charge accumulators P1 to P4, for example, the signal charge can be sufficiently isolated among the charge accumulators P1 to P4 that are adjacent. In other words, it is possible to suppress the inclusion of signal charge into other charge accumulators that are adjacent to the charge accumulator to which the signal charge is normally to be transferred.

In a configuration in which a plurality of transfer gate electrodes (in this case, the transfer gate electrodes Txa to Txd) are arranged within a pixel cell in such a way as to correspond to a plurality of charge accumulators (in this case, the charge accumulators P1 to P4), as depicted in FIG. 16, it is also possible for the charge accumulator that is closest to the photodiode 12 (in this case, the charge accumulator P1) to be used as a drain. For example, if the gate control voltage Vta is set to a high level at a certain time and thereafter and the gate between the charge transfer channel Ch1 and the charge accumulator P1 is opened, signal charge that flows into the charge transfer channel Ch1 at that time and thereafter is preferentially transferred to the charge accumulator P1. Therefore, if the gate control voltage Vta is set to a high level at a time and thereafter at which the gate control voltages Vtb to Vtd have been set to a high level and the gates between the charge transfer channel Ch1 and the charge accumulators P2 to P4 have been opened, it is possible to suppress the inclusion of excess charge into the charge accumulators P2 to P4. In the case where the charge accumulator P1 is to be used as a drain, it is not necessary for a reset to be performed prior to the detection of light in the charge accumulator P1.

It should be noted that in the configuration exemplified in FIG. 16, for example, the charge accumulator P2 and the charge accumulator Pa are arranged in line in the Y direction. However, it is not necessary for two charge accumulators that oppose each other on either side of the charge transfer channel Ch1 to be arranged in an aligned manner.

Modified Examples of Second Embodiment

Figure 19:
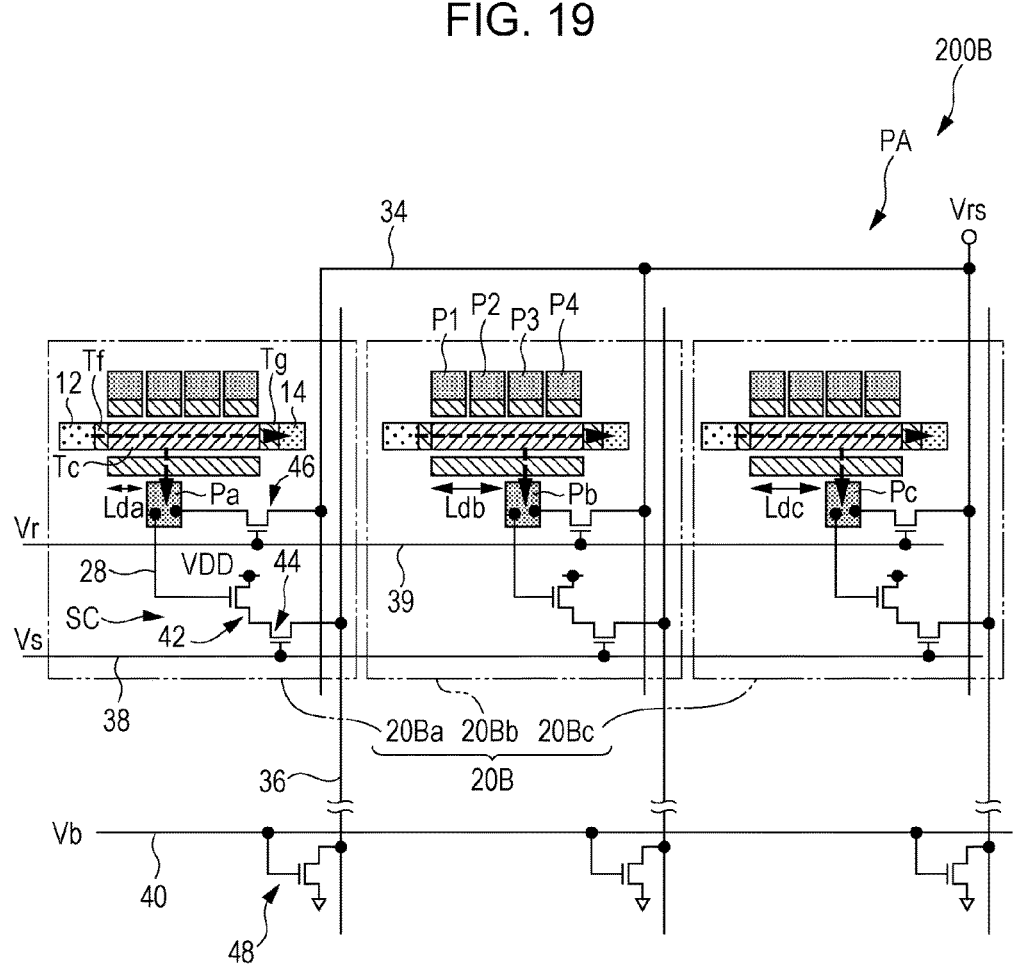
FIG. 19 is a plan view schematically depicting a first modified example of the imaging device according to the second embodiment.

FIG. 19 schematically depicts a first modified example of the imaging device according to the second embodiment. An imaging device 200B depicted in FIG. 19 has a pixel array PA that includes two or more pixel cells 20B having mutually different distances Ld from the photodiode 12 to the charge accumulator P. In this case, the three pixel cells 20Ba, 20Bb, and 20Bc that belong to the same row are depicted from among the plurality of pixel cells 20B. For example, the distance Ldb from the photodiode 12 to a charge accumulator Pb in the pixel cell 20Bb is approximately two times a distance Lda from the photodiode 12 to a charge accumulator Pa in the pixel cell 20Ba. Furthermore, a distance Ldc from the photodiode 12 to a charge accumulator Pc in the pixel cell 20Bc is approximately three times the distance Lda from the photodiode 12 to the charge accumulator Pa in the pixel cell 20Ba.

Figure 20:
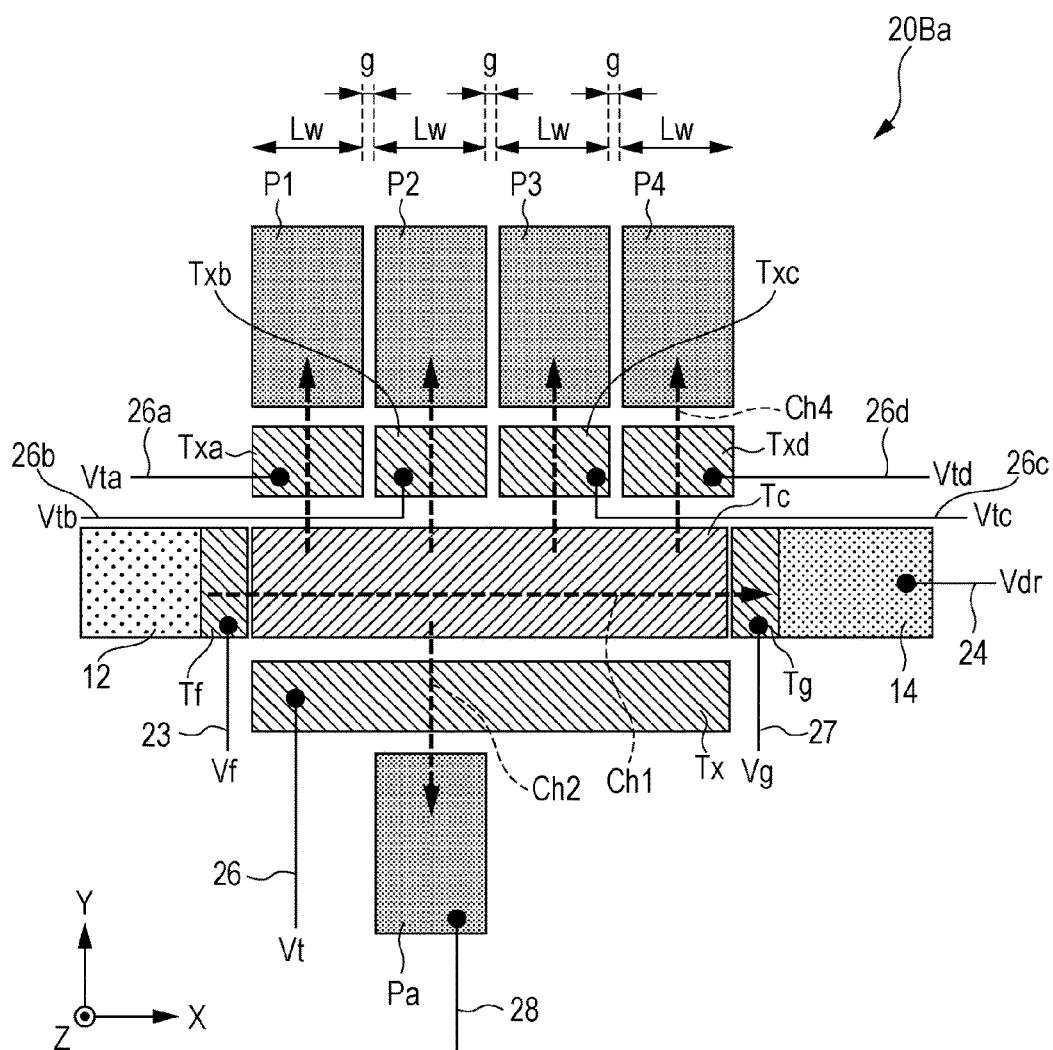
FIG. 20 is a plan view depicting an enlarged view of a pixel cell depicted in FIG. 19.

FIG. 20 depicts an enlarged view of the pixel cell 20Ba depicted in FIG. 19. The main points of difference between the pixel cell 20Ba depicted in FIG. 20 and the pixel cell 20Aa described with reference to FIG. 17 are that the pixel cell 20Ba has a transfer gate electrode Tf arranged between the photodiode 12 and the control electrode Tc, and a transfer gate electrode Tg arranged between the control electrode Tc and the drain 14. It should be noted that although the charge accumulators P1 to P4 in each of the pixel cells 20B may be connected to a reset voltage line that supplies a reset voltage, the charge accumulators P1 to P4 are not connected to the read-out lines 28a to 28d for reading out accumulated signal charge.

As mentioned above, the gate control line 23 is connected to the transfer gate electrode Tf. The transfer gate electrode Tf switches between transferring/not transferring signal charge from the photodiode 12 to the charge transfer channel Ch1, on the basis of the gate control voltage Vf applied to the gate control line 23. Meanwhile, a gate control line 27 is connected to the transfer gate electrode Tg. Similar to the gate control line 23, for example, the gate control line 27 is connected to the vertical scanning circuit 50 (see FIG. 1), and the potential of the gate control line 27 when the imaging device 100 is operating is controlled by the vertical scanning circuit 50. Typically, the transfer gate electrode Tg is arranged on the insulation layer 16 (see FIGS. 3 and 4) on the semiconductor substrate 2. The transfer gate electrode Tg makes up a portion of the gate that switches between transferring/not transferring signal charge from an end of the charge transfer channel Ch1 to the drain 14. By setting a gate control voltage Vg that is applied to the transfer gate electrode Tg via the gate control line 27 to a low level, for example, the transfer of signal charge from the charge transfer channel Ch1 to the drain 14 is stopped.

Reference will once again be made to FIG. 19. In this example, the read-out line 28 is connected to the charge accumulator P of each pixel cell 10B. Furthermore, each pixel cell 10B has a signal detection circuit SC that is connected to the read-out line 28. In this example, the signal detection circuit SC includes an amplification transistor 42 and an address transistor 44. The amplification transistor 42 and the address transistor 44 are typically field-effect transistors (FETs). Hereinafter, unless otherwise specified, an N-channel MOS is given as an example of a transistor.

The read-out line 28 is connected to the gate of the amplification transistor 42. During operation of the imaging device 200B, typically, a power source voltage VDD is supplied to the drain of the amplification transistor 42. The amplification transistor 42 outputs a signal that corresponds to the amount of signal charge accumulated in the charge accumulator P. In other words, the signal detection circuit SC reads out charge transferred to the charge accumulator P.

The address transistor 44 is connected between the source of the amplification transistor 42 and the vertical signal line 36. The vertical signal line 36 is provided for each column of the plurality of pixel cells 20B. An address control line 38 is connected to the gate of the address transistor 44. Typically, the address control line 38 is provided for each row of the plurality of pixel cells 20B and is connected to the vertical scanning circuit 50. A voltage Vs (may also be referred to as a row selection signal) that is applied to the address control line 38 is controlled by the vertical scanning circuit 50, and the row to be read out is thereby scanned and selected. A signal voltage is read out from the selected row of pixel cells 20B to the vertical signal line 36.

A load transistor 48 that constitutes a current source is connected to each vertical signal line 36. The gate of the load transistor 48 is connected to a voltage line 40 to which a predetermined bias voltage Vb is applied during operation of the imaging device 200B. The load transistor 48 may be part of the column circuit 52 (see FIG. 1). The load transistor 48 and the amplification transistor 42 constitute a source follower circuit.

Each of the pixel cells 20B is also connected to a reset voltage line 34 that supplies a reference voltage Vrs in the reset of the charge accumulator P. A reset transistor 46 is connected between the charge accumulator P of each pixel cell 20B and the reset voltage line 34. A reset signal line 39 is connected to the gates of the reset transistors 46. The reset signal line 39 is typically connected to the vertical scanning circuit 50. A voltage Vr (may also be referred to as a reset signal) that is applied to the reset signal line 39 is controlled by the vertical scanning circuit 50, and the potentials of the charge accumulators P of the pixel cells 20B are thereby reset in row units, for example. Although not depicted in order to avoid the drawing becoming complex, it should be noted that the reset transistor 46 is also connected to the charge accumulators P1 to P4. In other words, in the resetting of the charge accumulators P, the reference voltage Vrs is also supplied to the charge accumulators P1 to P4 via the reset transistor 46.

(Signal Detection Operation in Pixel Cells 20B)

Figure 21:
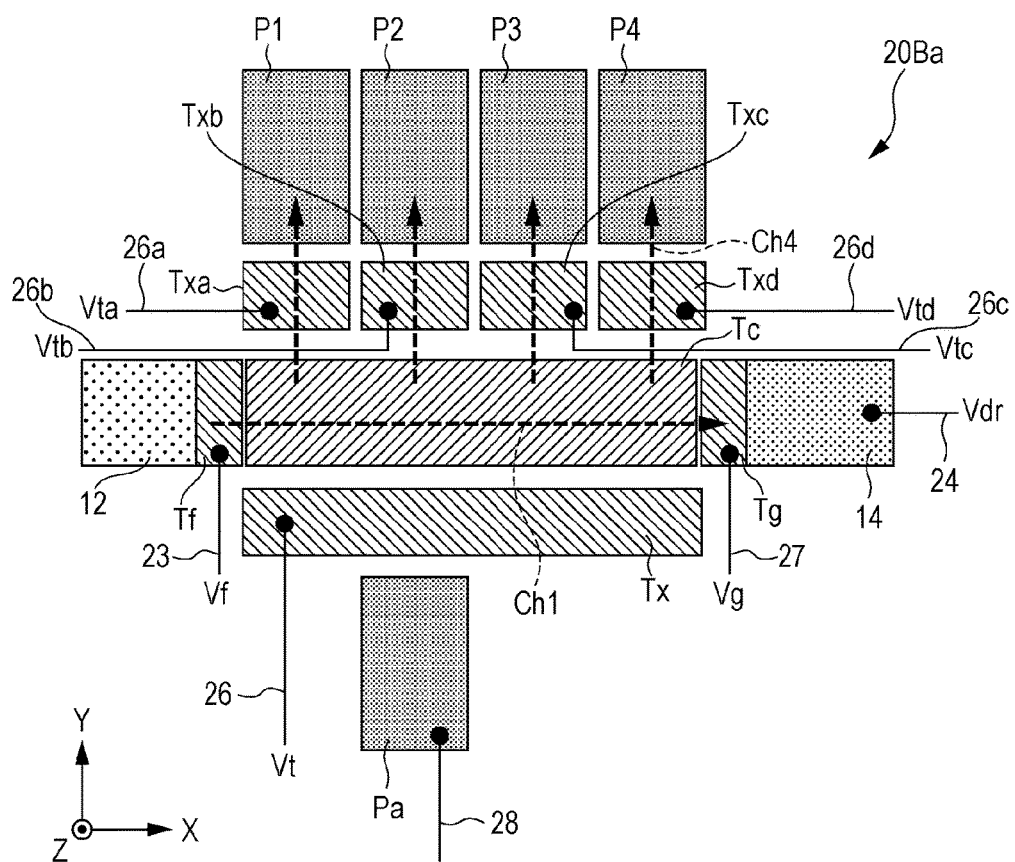
FIG. 21 is a plan view for illustrating an example of a signal detection operation in a pixel cell.
Figure 22:
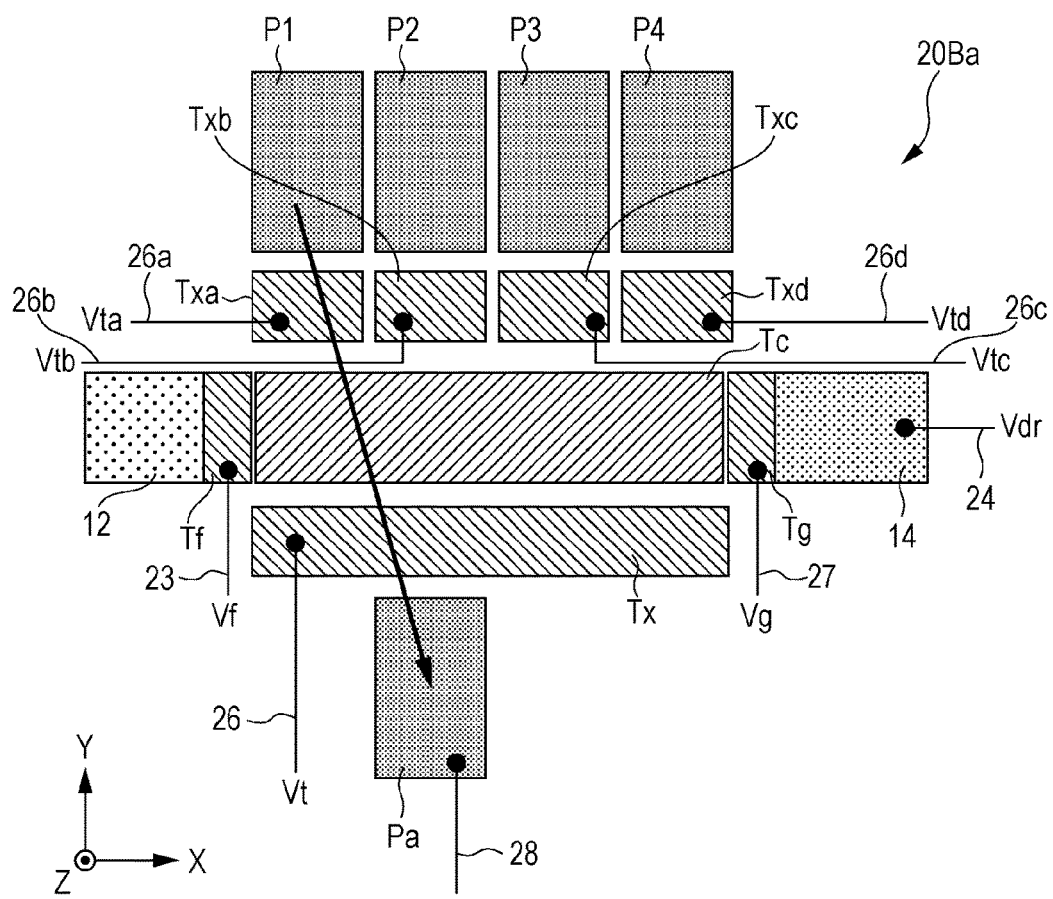
FIG. 22 is a plan view for illustrating an example of the signal detection operation in the pixel cell.
Figure 23:
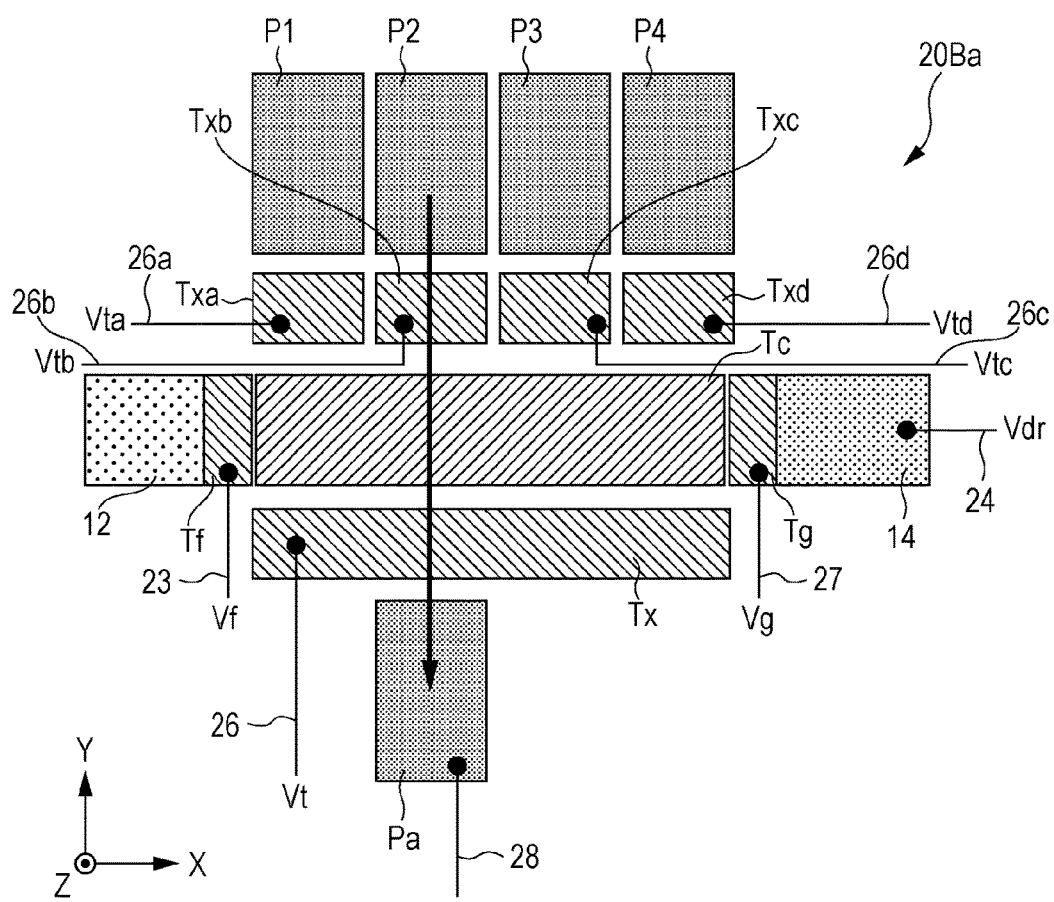
FIG. 23 is a plan view for illustrating an example of the signal detection operation in the pixel cell.

Next, an example of the signal detection operation in the pixel cell 20Ba will be described with reference to FIGS. 21 to 23. Schematically, after the signal charge within the charge transfer channel Ch1 has been transferred to the charge accumulators P1 to P4, the signal charge accumulated in each charge accumulator P1 to P4 is sequentially transferred to the charge accumulator Pa, and the charge transferred to the charge accumulator Pa is read out.

Prior to detection, first, the charge in each of the charge accumulators Pa and P1 to P4 is reset. Thereafter, exposure of the photodiode 12 to light is started, and, at a desired timing, the gate control voltage Vf applied to the transfer gate electrode Tf and the gate control voltage Vg applied to the transfer gate electrode Tg are set to a high level. The transfer of signal charge from the photodiode 12 to the drain 14 via the charge transfer channel Ch1 is thereby started at the desired timing.

After the start of the transfer of signal charge from the photodiode 12 to the drain 14, signal charge is transferred from the charge transfer channel Ch1 to the charge accumulators P1 to P4 via the charge transfer channels Ch4 (FIG. 21), in a similar manner to the detection operation described with reference to FIG. 18. Due to the transfer of signal charge via the charge transfer channels Ch4, the signal charge moving within the charge transfer channel Ch1 is distributed between the charge accumulators P1 to P4 in accordance with movement distance at the point in time when the gates between the charge transfer channel Ch1 and each of the charge accumulators P1 to P4 are opened. Thereafter, the gate control voltages Vta to Vtd that are applied to the transfer gate electrodes Txa to Txd are set to a low level, and the transfer of signal charge to the charge accumulators P1 to P4 is ended.

When the signal charge is transferred to the charge accumulators P1 to P4, the gate control voltage Vf applied to the transfer gate electrode Tf and the gate control voltage Vg applied to the transfer gate electrode Tg are a low level. By setting the gate control voltage Vf and the gate control voltage Vg to a low level, the gates between the photodiode 12 and the charge transfer channel Ch1 and between the charge transfer channel Ch1 and the drain 14 are closed, and the additional inflow of signal charge to the charge transfer channel Ch1 and the discharge of signal charge from the charge transfer channel Ch1 are stopped.

Thereafter, the gate control voltage Vta applied to the transfer gate electrode Txa and the gate control voltage Vt applied to the transfer gate electrode Tx are set to a high level. By switching the gate control voltage Vta and the gate control voltage Vt to a high level, the gate between the charge accumulator P1 and the charge transfer channel Ch1, and the gate between the charge transfer channel Ch1 and the charge accumulator Pa are opened. Due to these gates being opened, the signal charge accumulated in the charge accumulator P1 is transferred to the charge accumulator Pa via the charge transfer channel Ch4 that joins the charge accumulator P1 and the charge transfer channel Ch1, and the charge transfer channel Ch2 that joins the charge transfer channel Ch1 and the charge accumulator Pa, as schematically depicted by the thick solid arrow in FIG. 22. After the transfer of signal charge to the charge accumulator Pa, the gate between the charge accumulator P1 and the charge transfer channel Ch1, and the gate between charge transfer channel Ch1 and the charge accumulator Pa are closed. Thereafter, a signal corresponding to the amount of signal charge transferred to the charge accumulator Pa is read out by the aforementioned signal detection circuit SC.

Next, the reset transistor 46 is set to on and the charge transferred to the charge accumulator Pa is reset, and the reset transistor 46 is set to off. Thereafter, the gate control voltage Vtb applied to the transfer gate electrode Txb and the gate control voltage Vt applied to the transfer gate electrode Tx are set to a high level, and the signal charge accumulated in the charge accumulator P2 is transferred to the charge accumulator Pa (FIG. 23). The gate between the charge accumulator P2 and the charge transfer channel Ch1 and the gate between the charge transfer channel Ch1 and the charge accumulator Pa are closed, and thereafter the signal charge transferred to the charge accumulator Pa is read out via the signal detection circuit SC.

By repeating the aforementioned read-out operation also for the charge accumulator P3 and the charge accumulator P4, the signal charge accumulated in the charge accumulator P3 and the signal charge accumulated in the charge accumulator P4 can be sequentially read out by the signal detection circuit SC. In this way, in this example, signal charge moving within the charge transfer channel Ch1 toward the drain 14 is temporarily distributed between the charge accumulators P1 to P4 in accordance with the arrangement of the charge accumulators P1 to P4, and thereafter the signal charge accumulated in the charge accumulators P1 to P4 is sequentially transferred to the charge accumulator Pa, and the transferred signal charge is sequentially read out. The amount of signal charge distributed between the charge accumulators P1 to P4 corresponds to the four mutually different time windows. Consequently, according to this kind of control, it is possible for the reading-out of signals to be executed in a temporally separated manner while performing high-speed detection in four mutually different time windows.

Furthermore, according to a configuration in which the signal charge distributed between the charge accumulators P1 to P4 is transferred to the charge accumulator Pa and read out, it is not necessary to provide a signal detection circuit for each of the charge accumulators P1 to P4, and it is possible for the number of signal detection circuits SC to be provided for each pixel cell to be reduced to one. Consequently, a configuration in which the signal charge distributed between the charge accumulators P1 to P4 is transferred to the charge accumulator Pa and read out is advantageous for the miniaturization of pixel cells.

It should be noted that in the first modified example, the two or more pixel cells that have mutually different distances Ld from the photodiode 12 to the charge accumulator P in the direction along the charge transfer channel Ch1 do not necessarily have to be included. In other words, the pixel array PA may only have pixel cells of the same configuration as that of the pixel cell 20Ba depicted in FIG. 19, for example.

Figure 24:
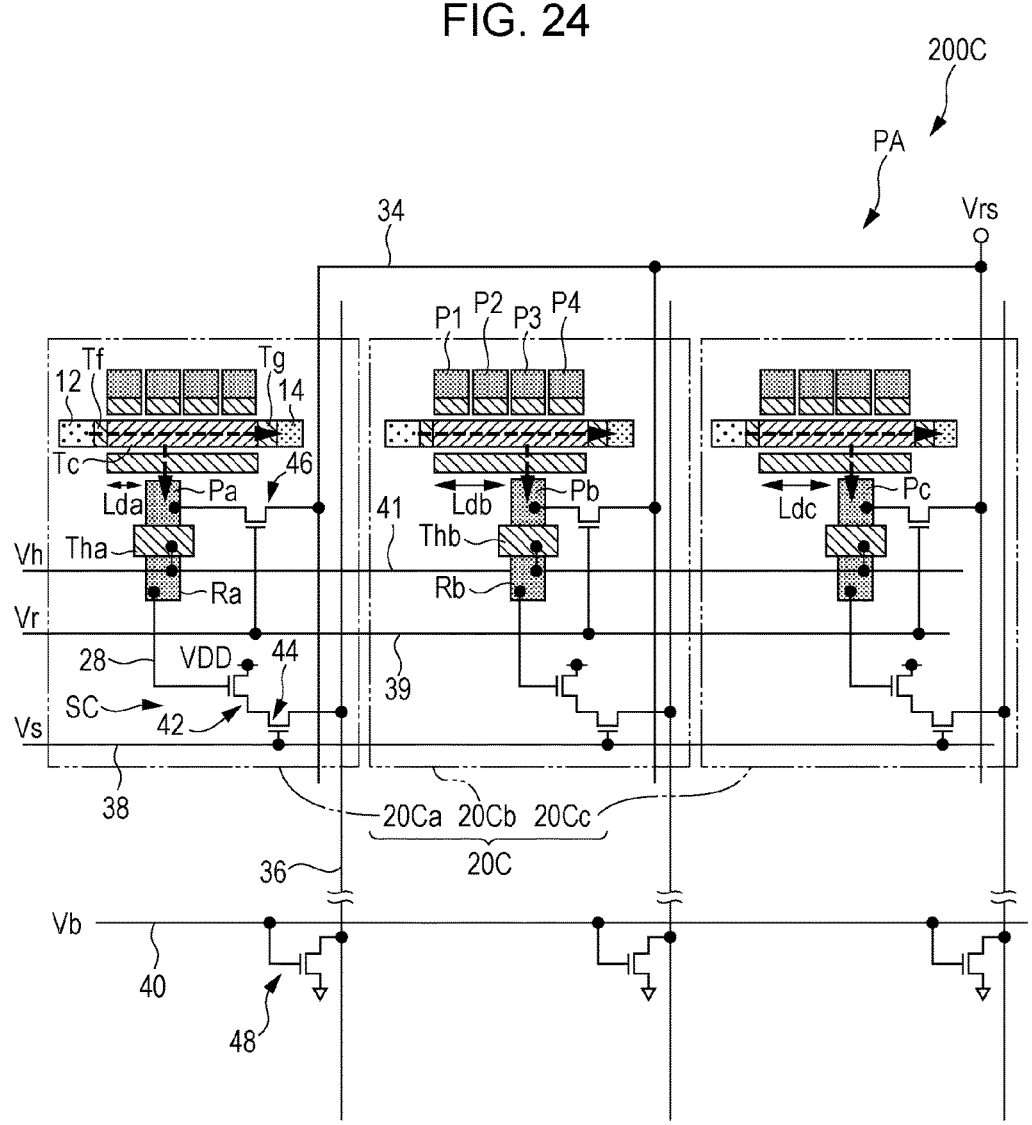
FIG. 24 is a plan view schematically depicting a second modified example of the imaging device according to the second embodiment.

FIG. 24 schematically depicts a second modified example of the imaging device according to the second embodiment. The pixel array PA in an imaging device 200C depicted in FIG. 24 includes two or more pixel cells 20C having mutually different distances Ld from the photodiode 12 to the charge accumulator P. In this case, the three pixel cells 20Ca, 20Cb, and 20Cc that belong to the same row are depicted from among the plurality of pixel cells 20C.

Attention will now be paid to the pixel cell 20Ca at the leftmost side of FIG. 24. The main points of difference between the pixel cell 20Ba depicted in FIG. 19 and the pixel cell 20Ca depicted in FIG. 24 are that the pixel cell 20Ca has a charge retaining unit Ra which is electrically connected to the read-out line 28, and a transfer gate electrode Tha which is arranged between the charge retaining unit Ra and the charge accumulator Pa. It should be noted that the pixel cell 20Cb and the pixel cell 20Cc also have the same configuration as the pixel cell 20Ca except that the distance from the photodiode 12 to the charge accumulator P is different. For example, the pixel cell 20Cb has a charge retaining unit Rb and a transfer gate electrode Thb.

As depicted in FIG. 24, the transfer gate electrode Tha is connected to a gate control line 41. The gate control line 41 is connected to the vertical scanning circuit 50 (see FIG. 1), for example, and the potential of the transfer gate electrode Tha is controlled by means of a voltage Vh supplied from the vertical scanning circuit 50 via the gate control line 41. Typically, the transfer gate electrode Tha is arranged on the insulation layer 16 (see FIGS. 3 and 4) on the semiconductor substrate 2.

The charge retaining unit Ra is typically an impurity region (an N-type region in this case) formed in the semiconductor substrate 2. By providing the transfer gate electrode Tha between the charge accumulator Pa and the charge retaining unit Ra, it is possible to form a gate that switches between transferring/not transferring signal charge from the charge accumulator Pa to the charge retaining unit Ra. That is, in this example, the transfer gate electrode Tha makes up a portion of a gate that switches between transferring/not transferring signal charge from the charge accumulator Pa to the charge retaining unit Ra.

It is known that thermal noise is generated together with the on and off operations of a transistor. For example, when thermal noise that accompanies the reset transistor 46 being set to off is large, there is a risk of the read-out signal deteriorating due to the inclusion of the thermal noise. Furthermore, when the retention period for signal charge in the charge accumulator Pa is long, there is a risk of the inclusion of noise caused by dark current. As described hereinafter, by providing the charge retaining unit Ra within the pixel cell 20Ca, it is possible to suppress the effect of noise such as thermal noise that accompanies the reset transistor 46 being set to off.

After the charge accumulator Pa has been reset by setting the reset transistor 46 on and off, the voltage Vh applied to the transfer gate electrode Tha is set to a high level, and the gate between the charge accumulator Pa and the charge retaining unit Ra is opened. The voltage Vh applied to the transfer gate electrode Tha is switched to a low level, and thereafter the charge within the charge retaining unit Ra is read out by the signal detection circuit SC. The level of the signal obtained at this time is a reset level that includes information regarding the thermal noise that accompanies the reset transistor 46 being set to off.

Thereafter, similar to the aforementioned signal charge read-out operation, signal charge is transferred to the charge accumulator Pa. For example, the signal charge accumulated in the charge accumulator P1 is first transferred to the charge accumulator Pa. If the gate between the charge accumulator Pa and the charge retaining unit Ra is opened after signal charge has been transferred to the charge accumulator Pa, the signal charge transferred to the charge accumulator Pa is transferred to the charge retaining unit Ra. Once the gate between the charge accumulator Pa and the charge retaining unit Ra has been closed, the signal charge transferred to the charge retaining unit Ra is read out by the signal detection circuit SC.

The signal obtained at this time has a level obtained by adding a voltage level corresponding to the amount of signal charge to the reset level. Consequently, by taking the difference between this signal level and the reset level, the original voltage level corresponding to the amount of signal charge is obtained with the effect of noise such as the thermal noise that accompanies a reset having been canceled.

It should be noted that after the signal charge accumulated in the charge accumulator P1 has been transferred to the charge accumulator Pa, for example, the signal charge accumulated in the charge accumulator P2 may be additionally transferred to the charge accumulator Pa. By transferring the signal charge accumulated in the charge accumulator P1 and the signal charge accumulated in the charge accumulator P2 to the charge accumulator Pa and then executing transfer to the charge retaining unit Ra, it is possible to obtain a signal level that corresponds to the sum of these amounts of signal charge. In other words, it is possible for the width of the time window in detection to be enlarged retrospectively.

Alternatively, in the case where the charge traveling within the charge transfer channel Ch1 is transferred to the charge accumulator Pa via the charge transfer channel Ch2 without using the charge accumulators P1 to P4, a cycle that includes transferring signal charge from the charge transfer channel Ch1 to the charge accumulator Pa and transferring signal charge from the charge accumulator Pa to the charge retaining unit Ra may be executed a plurality of times. An integrated signal level is obtained by reading out the amount of charge finally accumulated in the charge retaining unit Ra after having executed transfer a plurality of times. Consequently, it is possible to obtain a sufficiently large signal level even if the amount of signal charge transferred via the charge transfer channel Ch2 in each cycle is a minute amount.

It should be noted that in the second modified example, the two or more pixel cells that have mutually different distances Ld from the photodiode 12 to the charge accumulator P in the direction along the charge transfer channel Ch1 do not necessarily have to be included. In other words, the pixel array PA may only have pixel cells of the same configuration as that of the pixel cell 20Ca depicted in FIG. 24, for example.

Figure 25:
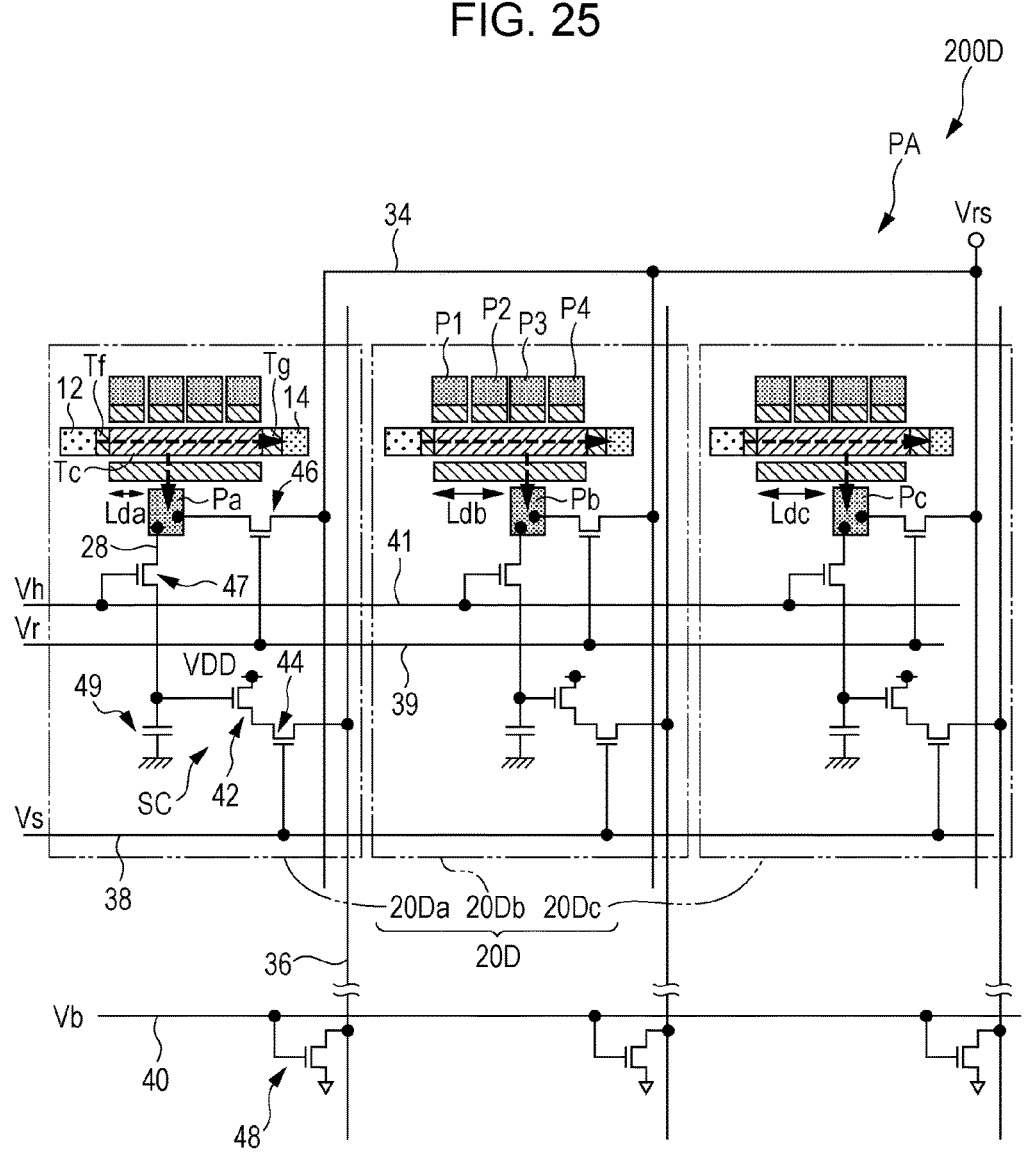
FIG. 25 is a plan view schematically depicting a third modified example of the imaging device according to the second embodiment.

FIG. 25 schematically depicts a third modified example of the imaging device according to the second embodiment. The pixel array PA in an imaging device 200D depicted in FIG. 25 includes two or more pixel cells 20D having mutually different distances Ld from the photodiode 12 to the charge accumulator P. In this case, the three pixel cells 20Da, 20Db, and 20Dc that belong to the same row are depicted from among the plurality of pixel cells 20D.

Attention will now be paid to the pixel cell 20Da at the leftmost side of FIG. 25. The main points of difference between the pixel cell 20Ca depicted in FIG. 24 and the pixel cell 20Da depicted in FIG. 25 are that, in the pixel cell 20Da, the read-out line 28 is connected to the charge accumulator Pa, and a transfer transistor 47 is connected between the read-out line 28 and the amplification transistor 42. Furthermore, a capacitor 49 having one end grounded is connected between the gate of the amplification transistor 42 and the transfer transistor 47. As depicted in the drawing, the gate of the transfer transistor 47 is connected to the gate control line 41, and setting the transfer transistor 47 on and off is controlled by means of the voltage Vh applied to the gate control line 41.

As depicted in FIG. 25, the set of the transfer transistor 47 and the capacitor 49 is used instead of the set of the transfer gate electrode Tha and the charge retaining unit Ra. A detection operation similar to that of the second modified example is possible also with this kind of configuration. The transfer transistor 47 has the function of serving as a gate that switches between transferring/not transferring signal charge from the charge accumulator Pa to the capacitor 49, and the capacitor 49 has the function of temporarily accumulating signal charge transferred from the charge accumulator Pa.

In this way, the element that temporarily accumulates the signal charge transferred from the charge accumulator Pa is not restricted to junction capacitance formed by a pn junction. A metal-insulator-metal (MIM) structure, a metal-oxide-metal (MOM) structure, a depletion-type MOS (DMOS), or the like can be applied as the structure of the capacitor 49. It should be noted that in the semiconductor substrate 2 (see FIG. 1), the main surface on the light-receiving region side of the photodiode 12 and the main surface on which the electrodes such as the control electrode Tc, the wiring, and the like are formed may be different. In the case where this kind of so-called rear-surface irradiation type of structure is adopted, by employing a MIM structure and a MOM structure, it is possible to effectively utilize the region in which the electrodes, wiring, and the like are formed in the pixel cells. It should be noted that in the case where an organic photoelectric conversion film is used as the photoelectric converter 12, it is possible to apply a configuration similar to a stacked imaging device so to speak, in which a photoelectric converter is arranged on an interlayer insulation layer that covers a semiconductor substrate. In this kind of configuration, by applying a DMOS structure as the structure of the capacitor 49, it is possible to effectively utilize the region on the semiconductor substrate 2 and the region within the interlayer insulation layer including the wiring layer.

It should be noted that in the third modified example, the two or more pixel cells that have mutually different distances Ld from the photodiode 12 to the charge accumulator P in the direction along the charge transfer channel Ch1 do not necessarily have to be included. In other words, the pixel array PA may only have pixel cells of the same configuration as that of the pixel cell 20Da depicted in FIG. 25, for example.

As described hereinabove, in the embodiments of the present disclosure, rather than signal charge being directly transferred from the photoelectric converter to the charge accumulator and the transferred charge being read out, the signal charge that moves from the photoelectric converter to the drain is transferred from that movement channel to the charge accumulator. Consequently, temporal resolution corresponding to the distance that the signal charge moves from photoelectric converter is possible, and temporal resolution in detection can be improved.

In addition, in the aforementioned embodiments, the pixel array PA includes pixel cells having mutually different distances between the photoelectric converter 12 and the charge accumulator P in the direction in which the photoelectric converter 12 and the drain 14 are joined. Consequently, it is possible for detection in time windows that start at different times to be executed collectively with a single exposure. For example, it is possible for a plurality of items of image data corresponding to the different times to be acquired with one instance of imaging.

The technology of the present disclosure is not restricted to the aforementioned embodiments, and various alterations are possible. For example, a diode having a structure in which a plurality of sensors having different wavelength bands of sensitivity are stacked in the thickness direction of a substrate (for example, a Foveon X3 (registered trademark) provided by Foveon, Inc.) may be used as the photodiode 12. Each of the aforementioned amplification transistor 42, address transistor 44, reset transistor 46, transfer transistor 47, and load transistor may be an N-channel MOS or a P-channel MOS. It is not necessary for all of these to be uniformly N-channel MOSs or P-channel MOSs.

The photoelectric converter in the present disclosure is not restricted to a photodiode. A photoelectric conversion film laminated on a semiconductor substrate can also be used instead of the photodiode 12. A photoelectric conversion film can be formed from an organic material or an inorganic material such as amorphous silicon.

It is possible for the imaging element of the present disclosure to be used in various camera systems and sensor systems, such as digital still cameras, medical cameras, surveillance cameras, vehicle-mounted cameras, digital single-lens reflex cameras, and digital mirrorless single-lens cameras.

What is claimed is:

1. An imaging device comprising a first pixel cell and a second pixel cell, wherein
   the first pixel cell includes:
      a first photoelectric converter that generates first charge;
      a first charge transfer channel that has a first end electrically connected to the first photoelectric converter, and a second end, the first charge transfer channel transferring the first charge in a first direction from the first end toward the second end;
      a second charge transfer channel that branches from a first position of the first charge transfer channel, the second charge transfer channel transferring at least a part of the first charge; and
      a first charge accumulator that accumulates charge transferred via the second charge transfer channel,
   the second pixel cell includes:
      a second photoelectric converter that generates second charge;
      a third charge transfer channel that has a third end electrically connected to the second photoelectric converter, and a fourth end, the third charge transfer channel transferring the second charge in a second direction from the third end toward the fourth end;
      a fourth charge transfer channel that branches from a second position of the third charge transfer channel, the fourth charge transfer channel transferring at least a part of the second charge; and
      a second charge accumulator that accumulates charge transferred via the fourth charge transfer channel, and
   a distance from the first end to the first position in the first direction is different from a distance from the third end to the second position in the second direction.

2. The imaging device according to claim 1, wherein
   the first pixel cell includes a first gate that switches between transferring and blocking the at least the part of the first charge to the second charge transfer channel, and
   the second pixel cell includes a second gate that switches between transferring and blocking the at least the part of the second charge to the fourth charge transfer channel.

3. The imaging device according to claim 2, further comprising
   a controller that causes the first gate and the second gate to be changed from blocking to transferring at a same timing.

4. The imaging device according to claim 2, wherein
   the first gate includes a first gate electrode located on the second charge transfer channel,
   the second gate includes a second gate electrode located on the fourth charge transfer channel, and
   the first gate electrode is electrically connected to the second gate electrode.

5. The imaging device according to claim 1, wherein
   the first pixel cell includes a first gate that switches between transferring and blocking charge from the first photoelectric converter to the first charge transfer channel, and
   the second pixel cell includes a second gate that switches between transferring and blocking charge from the second photoelectric converter to the third charge transfer channel.

6. The imaging device according to claim 1, wherein
   the first pixel cell includes a first drain electrically connected to the second end of the first charge transfer channel, and
   the second pixel cell includes a second drain electrically connected to the fourth end of the third charge transfer channel.

7. The imaging device according to claim 1, wherein
   the first pixel cell includes:
      a first drain electrically connected to a third position of the first charge transfer channel; and
      a first gate that switches between transferring and blocking charge from the third position to the first drain,
   the second pixel cell includes:
      a second drain electrically connected to a fourth position of the second charge transfer channel; and
      a second gate that switches between transferring and blocking charge from the fourth position to the second drain,
   a distance from the first end to the third position in the first direction is the same as a distance from the third end to the fourth position in the second direction,
   a distance from the first end to the third position in the first direction is less than a distance from the first end to the first position in the first direction, and
   a distance from the third end to the fourth position in the second direction is less than a distance from the third end to the second position in the second direction.

8. The imaging device according to claim 1, wherein
   the first pixel cell includes a third charge accumulator that is electrically connected to the second end of the first charge transfer channel, the third charge accumulator accumulating charge transferred via the first charge transfer channel, and
   the second pixel cell includes a fourth charge accumulator that is electrically connected to the fourth end of the third charge transfer channel, the fourth charge accumulator accumulating charge transferred via the third charge transfer channel.

9. The imaging device according to claim 1, wherein
   the first pixel cell includes:
      a fifth charge transfer channel that branches from a third position of the first charge transfer channel, the fifth charge transfer channel transferring at least a part of the first charge;
      a first gate that switches between transferring and blocking charge in the fifth charge transfer channel;
      a third charge accumulator that accumulates charge transferred via the fifth charge transfer channel;
      a sixth charge transfer channel that branches from a fourth position of the first charge transfer channel, the sixth charge transfer channel transferring at least a part of the first charge;

a second gate that switches between transferring and blocking charge in the sixth charge transfer channel; and a fourth charge accumulator that accumulates charge transferred via the sixth charge transfer channel, and a distance from the first end to the third position in the first direction is different from a distance from the first end to the fourth position in the first direction.

10. The imaging device according to claim 9, wherein the first charge transfer channel is located, in plan view, between the third and fourth charge accumulators and the first charge accumulator.

11. The imaging device according to claim 9, wherein the first pixel cell includes:
   a third gate that switches between transferring and blocking the first charge from the first photoelectric converter to the first charge transfer channel;
   a first drain electrically connected to the second end of the first charge transfer channel; and
   a fourth gate that is located between the first charge transfer channel and the first drain, the fourth gate switching between transferring and blocking charge from the first charge transfer channel to the first drain.

12. The imaging device according to claim 9, wherein the first pixel cell includes:
   a fifth charge accumulator electrically connected to the first charge accumulator;
   a third gate that switches between transferring and blocking charge accumulated in the first charge accumulator from the first charge accumulator to the fifth charge accumulator; and
   a read-out circuit electrically connected to the fifth charge accumulator.

13. The imaging device according to claim 9, wherein the first pixel cell includes:
   a capacitor electrically connected to the first charge accumulator; and
   a read-out circuit electrically connected to the first charge accumulator.

14. The imaging device according to claim 1, comprising first pixel cells and second pixel cells, the first pixel cell being one of the first pixel cells, the second pixel cell being one of the second pixel cells, wherein
   the first pixel cells and the second pixel cells are arranged two-dimensionally in a row direction and a column direction,
   the first pixel cells are arranged in one of the row direction and the column direction, and
   the second pixel cells are arranged in the one of the row direction and the column direction.

15. The imaging device according to claim 1, wherein
   the first charge transfer channel does not have a gate between the first end and the second end, and
   the second charge transfer channel does not have a gate between the third end and the fourth end.

* * * * *